US006946439B2

(12) United States Patent
Hembrough et al.

(10) Patent No.: US 6,946,439 B2
(45) Date of Patent: Sep. 20, 2005

(54) COMPOSITIONS AND METHODS FOR INHIBITING CELLULAR PROLIFERATION COMPRISING TFPI FRAGMENTS

(75) Inventors: Todd Hembrough, Damascus, MD (US); Victor P. Pribluda, Silver Spring, MD (US); Adonia E. Papathanassiu, Silver Spring, MD (US); Shawn J. Green, Vienna, VA (US)

(73) Assignee: Entre Med, Inc., Rockville, MD (US)

( * ) Notice: Subject to any disclaimer, the term of this patent is extended or adjusted under 35 U.S.C. 154(b) by 40 days.

(21) Appl. No.: 10/086,176

(22) Filed: Feb. 28, 2002

(65) Prior Publication Data

US 2002/0173465 A1 Nov. 21, 2002

Related U.S. Application Data

(63) Continuation-in-part of application No. 09/766,778, filed on Jan. 22, 2001, now Pat. No. 6,734,163, which is a continuation of application No. 09/227,955, filed on Jan. 11, 1999, now abandoned, which is a continuation of application No. 08/796,850, filed on Feb. 6, 1997, now Pat. No. 5,981,471, application No. 10/086,176, which is a continuation-in-part of application No. 09/130,273, filed on Aug. 6, 1998, now abandoned, which is a continuation-in-part of application No. 08/796,850.

(51) Int. Cl.[7] ............................................... A61K 38/16
(52) U.S. Cl. ............................... 514/2; 514/12; 514/13
(58) Field of Search .............................. 514/2, 25, 13

(56) References Cited

U.S. PATENT DOCUMENTS

| 4,552,888 A | 11/1985 | Koppel et al. |
| 4,994,443 A | 2/1991 | Folkman et al. |
| 5,001,116 A | 3/1991 | Folkman et al. |
| 5,021,404 A | 6/1991 | Folkman et al. |
| 5,223,409 A | 6/1993 | Ladner et al. |
| 5,358,959 A | 10/1994 | Halperin et al. |
| 5,385,885 A | 1/1995 | Gasic et al. |
| 5,589,359 A | 12/1996 | Innis et al. |
| 5,653,744 A | 8/1997 | Khouri |
| 5,770,563 A | 6/1998 | Roberts et al. |
| 5,795,865 A | 8/1998 | Markland et al. |
| 5,981,471 A | 11/1999 | Papathanassiu et al. |
| 6,010,880 A | 1/2000 | Markland et al. |

FOREIGN PATENT DOCUMENTS

| WO | WO 97/35609 | 2/1997 |
| WO | WO 97/09063 | 3/1997 |

OTHER PUBLICATIONS

Algire, G.H. et al., Vascular reactions of normal and malignant tumors in vivo. I. Vascular reactions of mice to wounds and to normal and neoplastic transplants, *Journal of the National Cancer Institute* Vol/Iss: 6, pp. 73–85, Aug. 1945.

Bok, R.A. et al., Quantiative Characterization of the Binding of Plasminogen to Intact Fibrin Clots, Lysine–Sepharose, and Fibrin Cleaved by Plasmin, *Biochemistry* , Vol/Iss: 24, pp. 3279–3286, 1985.

Brem, H. et al., Title: Interstitial chemotherapy with drug polymer implants for the treatment of recurrent gliomas, *Journal of Neurosurgery*, Vol/Iss: 74, pp. 441–446, Mar. 1, 1991.

Broze et al., Regulation of Coagulation by a Multivalent Kunitz–Type Inhibitor, *Biochemistry*, Vol/Iss: 29(33), pp. 7539–7546, Aug. 21, 1990.

Broze, G.J., Jr. et al., Tissue Factor Pathway Inhibitor and the Revised Theory of Coagulation, *Annu. Rev. Med.*, Vol/Iss: 46, pp.: 103–112, 1995.

Cao, Y. et al., gro–B, a–C–X–C–Chemokine, is an Angiogenesis Inhibitor that Suppresses the Growth of Lewis Lung Carninoma in Mice, *Journal of Experimental Medicine*, Vol/Iss: 182, pp. 2069–2077, Dec. 1, 1995.

Cao, Y. et al., Kringle Domains of Human Angiostatin, *The Journal of Biological Chemistry*, Vol/Iss: 271(46), pp. 29461–29467, Nov. 15, 1996.

Cardiff, R.D., Protoneoplasia: The Molecular Biology of Murine Mammary Hyperplasia (Abstract only), *Advances in Cancer Research*, Vol/Iss: 42, pp. 167–190, Jan. 1, 1984.

Chen, C. et al., Title: A Strategy to Discover Circulating Angiogenesis Inhibitors Generated by Human Tumors, *Cancer Research*, Vol/Iss: 55, pp. 4230–4233, Oct. 1, 1995.

Clements et al., Title: Kallikreins and kinins in inflammatory–like events in the reproductive tract (Abstract only), *Pharmacological Research*, Vol/Iss: 35(6), pp. 537–540, Jun. 1997.

Contrino, J., In situ detection of tissue factor in vascular endothelial cells: Correlation with the malignant phenotype of human breast disease, *Nature Medicine*, Vol/Iss: 2(2), pp. 209–215, Feb. 1996.

Crum, R. et al., Title: A New Class of Steroids Inhibits Angiogenesis in the Presence of Heparin or a Heparin Fragment, *Science*, Vol/Iss: 230, pp. 1375–1378, Dec. 20, 1985.

(Continued)

*Primary Examiner*—Michael Borin
(74) *Attorney, Agent, or Firm*—Kilpatrick Stockton LLP

(57) ABSTRACT

Compositions and methods effective in inhibiting abnormal or undesirable cell proliferation, particularly endothelial cell proliferation and angiogenesis related to neovascularization and tumor growth are provided. The compositions comprise a naturally occurring or synthetic protein, peptide, or protein fragment containing all or an active portion of the C-terminal portion of proteinase inhibitors such as TFPI. The methods involve administering to a human or animal the composition described herein in a dosage sufficient to inhibit cell proliferation, particularly endothelial cell proliferation. The methods are useful for treating diseases and processes mediated by undesired and uncontrolled cell proliferation, such as cancer, particularly by inhibiting angiogenesis. Administration of the composition to a human or animal having prevascularized, metastasized tumors is useful for preventing the growth or expansion of such tumors.

18 Claims, 15 Drawing Sheets

OTHER PUBLICATIONS

Davies et al., Title: Pathobiology of Intimal Hyperplasia, *British Journal of Surgery*, Vol/Iss: 81(4), pp. 1254–1269, Sep. 1994.

Devaraj et al., Title: The effects of alpha–tocopherol on critical cells in atherogenesis, *Current Opinion in Lipidology*, Vol/Iss: 9(1), pp. 11–15, Feb. 1998.

Dinbergs et al., Cellular Response to Transforming Growth Factor–β1 and Basic Fibroblast Growth Factor Depends on Release Kinetics and Extracellular Matrix Interactions, *The Journal of Biological Chemistry*, Vol/Iss: 271(47), pp. 29822–29829, Nov. 22, 1996.

Enjyoji, K. et al., Effect of Heparin on the Inhibition of Factor Xa by Tissue Factor Pathway Inhibitor: A Segment, $Gly^{212}$—$Phe^{243}$, of the third Kunitz Domain is a Heparin–Binding Site, *Biochemistry*, Vol/Iss: 34(17), pp. 5725–5735, 1995.

Ferenczy, A. et al., The cytodynamics of endometrial hyperplasia and carcinoma, *Annales de Pathologie*, Vol/Iss: 3(3), pp. 189–201, Sep. 1983.

Folkman, J., Tumor angiogenesis and tissue factor, *Nature Medicine*, Vol/Iss: 2, pp. 167–168, Feb, 1, 1996.

Folkman, J., What is the Evidence that Tumors are Angiogenesis Dependent?, *Journal of the National Cancer Institute*, Vol/Iss: 82, pp. 4–6, Jan. 3, 1990.

Folkman, J., Angiogenesis in cancer, vascular, rheumatoid and other disease, *Nature Medicine*, Vol/Iss:1(1), pp. 27–31, Nov. 1, 1995.

Folkman, J., Angiogenesis and Its Inhibitors, *Important Advances in Oncology*, Vol/Iss: , pp. 42–62, 1985.

Folkman, J., Tumor Angiogenesis: Therapeutic Implications, *New England Journal of Medicine*, Vol/Iss: 285 (21), pp. 1182–1186, Nov. 18, 1971.

Folkman, J. et al., Long–term culture of capillary endothelial cells, *Proceedings of the National Academy of Science USA*, Vol/Iss: 76, pp. 5217–5221, Oct. 1, 1979.

Folkman, J. et al., Induction of angiogenesis during the transition from hyperplasia to neoplasia, *Nature*, Vol/Iss: 339, pp. 58–61, May 4, 1989.

Folkman, J. et al., Tumor Behavior in Isolated Perfused Organs in vitro Growth and Metastases of Biopsy Material in Rabbit Thyroid and Canine Intestinal Segment, *Annals of Surgery*, Vol/Iss: 164(3), pp. 491–502, Sep. 1, 1966.

Gimbrone, M.A. et al., Tumor growth and neovascularization: An experimental model using the rabbit cornea, *Journal of the National Cancer Institute*, Vol/Iss: 52(2), pp. 413–427: Feb. 1974.

Gimbrone, M.A. et al., Tumor dormancy in vivo by Prevention of Neovascularization, *Journal of Experimental Medicine*, Vol/Iss: 136, pp. 261–276, 1972.

Good, D.J. et al., A tumor suppressor–dependent inhibitor of angiogenesis is immunologically and functionally indistinguishable from a fragment of thombospondin, *Proceedings of the National Academy of Science USA*, Vol/Iss: 87, pp. 6624–6628, Sep. 1990.

Gross, J.L. et al., Modulation of Solid Tumor Growth in vivo by bFGF (Abstract only), *Proceedings of the American Association of Cancer Research*, Vol/Iss: 31, pp. 79, Mar. 1990.

Gupta, S. et al., A potent inhibitor of endothelial cell proliferation is generated by proteolytic cleavage of the chemokine platelet factor 4, *Proceedings of the National Academy of Science USA*, Vol/Iss: 92, pp. 7799–7803, Aug. 1995.

Haas, A.F. et al., Angiolymphoid Hyperplasia with Eosinophila of the Hand, *Journal of Dermatologic Surgery and Oncology*, Vol/Iss: 17, pp. 731–734, Sep. 1991.

Hanada et al., Carboxyl Terminal Basic Amino Acid Region of TFPI Prevents Proliferation of Human Smooth Muscle Cells by Inhibiting Activation of Map Kinase Kinase ( Abstract only), *Thrombosis and Haemostatis, Supplement*, Jul. 2001.

Holmgren, L. et al., Dormancy of micrometastases: Balanced proliferation and apoptosis in the presence of angiogenesis suppression, *Nature Medicine*, Vol/Iss: 1(2), pp. 149–153, Feb. 1995.

Homandberg, G.A. et al., Heparin–binding Fragments of Fibronectin are Potent Inhibitors of Endothelial Cell Growth, *American Journal of Pathology*, Vol/Iss: 120, pp. 327–332, Sep. 1985.

Ingber, D. et al., Synthetic analogues of fumagillin that inhibit angiogenesis and suppress tumor growth, *Nature*, Vol/Iss: 348, pp. 555–557, Dec. 6, 1990.

Ishino et al., An Autopsy Case of Cerebral Form of v. Winlwarter–Buerger's Disease with a Chronic Course of 12 Years, *Folia Psychiatrica Neurologica Japonica*, Vol/Iss: 27(3), pp. 207–221, 1973.

Kamikubo, Y. et al., Human Recombinant Tissue–Factor Pathway Inhibitor Prevents the Proliferation of Cultured Human Neonatal Aortic Smooth Muscle Cells, *FEBS Letters*, Vol/Iss: 407, pp. 116–120, Jan. 1, 1997.

Kehrel, B., Platelet–collagen interactions, *Seminars in Thrombosis and Hemostasis*, Vol/Iss: 21(2), pp. 123–129, 1995.

Khouri, R.K. et al., Local Application of Tissue Factor Pathway Inhibitor (TFPI) Inhibits Intimal Hyperplasia Induced by Arterial Interventions, *Surgical Forum*, Vol/Iss: 46, pp. 389–391, 1995.

Kim, K.J. et al., Inhibition of vascular endothelial growth factor–induced angiogenesis suppresses tumor growth in Vivo, *Nature*, Vol/Iss: 362, pp. 841–844, Apr. 29, 1993.

Knighton, D. et al., Avascular and Vascular Phases of Tumour Growth in the Chick Embyo, *British Journal of Cancer*, Vol/Iss: 35, pp. 347–356, 1977.

Korff et al., Integration of Endothelial Cells in Multicellular Spheroids Prevents Apoptosis and Induces Differentiation, *The Journal of Cell Biology*, Vol/Iss: 143 (5), pp. 1341–1352, Nov. 30, 1998.

Korff et al., Blood vessel maturation in a 3–dimensional spheroidal coculture model: direct contact with smooth muscle cells regulates endothelial cell quiescence and abrogates VEGF responsiveness, *The FASEB Journal*, Vol/Iss: 15, pp. 447–457, Feb. 2001.

Korff et al., Title: Tensional forces in fibrillar extracellular matrices control directional capillary sprouting, *Journal of Cell Science*, Vol/Iss: 112 (19), pp. 3249–3258, Oct. 1999.

Koyama et al., Regulation and Function of an Activation–Dependent Epitope of the β1 Integrins in Vascular Cells after Balloon Injury in Baboon Arteries and in Vitro, *American Journal of Pathology*, Vol/Iss: 148(3), pp. 749–761, Mar. 1996.

Kuzuya et al., Antioxidants Stimulate Endothelial Cell Proliferation in Culture, *Artery*, Vol/Iss: 18 (3), pp. 115–124, 1991.

Lindahl, A., Coagulation Inhibition and Activation in Pancreatic Cancer, *Cancer*, Vol/Iss: 70 (80), pp. 2067–2072, Oct. 15, 1992.

Lupu, C. et al., Thrombin Induces the Redistribution and Acute Release of Tissue Factor Pathway Inhibitor from Specific Granules within Human Endothelial Cells in Culture, *Arteriosclerosis, Thrombosis, and Vascular Biology*, Vol/Iss: 15(11), pp. 2055–2062, Nov. 1995.

Maione, T.E. et al., Inhibition of Angiogenesis by Recombinant Human Platelet Factor–4 and Related Peptides, *Science*, Vol/Iss: 247, pp. 77–79, Jan. 5, 1990.

McGee, J. et al., Simultaneous Expression of Tissue Factor and Tissue Factor Pathway Inhibitor by Human Monocytes. A Potential Mechanism for Localized Control of Blood Coagulation, *Journal of Experimental Medicine*, Vol/Iss: 179, pp. 1847–1854, Jun. 1, 1994.

Miyagi, Y. et al., cDNA Cloning and mRNA Expression of a Serine Protease Inhibitor Secreted by Cancer Cells: Identification as Placental Protein 5 and Tissue Factor Pathway Inhibitor–2, *Journal of Biochemistry*, Vol/Iss: 116, pp. 939–942, 1994.

Moss, G.W. et al., Hypothesis for a serine–protease–like domain at the COOH terminus of *Slowpoke* calcium–activated potassium channels., *Journal of General Physiology*, Vol/Iss: 108 (6), pp. 473–484, Dec. 1996.

Nakao–Hayashi et al., Stimulatory effects of insulin and insulin–like growth factor I on migration and tube formation by vascular endothelial cells, *Atherosclerosis*, Vol/Iss: 92, pp. 141–149, Feb. 1992.

Narita, M. et al., Two Receptor Systems are Involved in the Plasma Clearance of Tissue Factor Pathway Inhibitor in vivo, *Journal of Biological Chemistry*, Vol/Iss: 270 (42), pp. 24800–24804, Nov. 20, 1995.

Nguyen, M. et al., Quantitation of Angiogenesis and Anti-angiogenesis in the Chick Embryo Chorioallantoic Membrane, *Microvascular Research*, Vol/Iss: 47, pp. 31–40, 1994.

Nguyen, M. et al., Elevated Levels of the Angiogenic Peptide Basic Fibroblast Growth Factor in Urine of Bladder Cancer Patients, *Journal of the National Cancer Institute*, Vol/Iss: 85 (3), pp. 241–242, Feb. 3, 1993.

Niwano et al., Inhibitory action of amyloid precursor protein against human Hagemanb factor (factor XII), *Journal of Laboratory Clinical Medicine*, Vol/Iss: 125 (2), pp. 252–256, Feb. 1995.

Novotny, W.F. et al., Purification and Characterization of the Lipoprotein–Associated Coagulation Inhibitor from Human Plasma, *Journal of Biological Chemistry*, Vol/Iss: 264, pp. 18832–18837, Nov. 5, 1989.

O'Reilly et al., Endogenous Inhibitors of Angiogenesis (Abstract only), *Proceedings of the American Association of Cancer Research*, Vol/Iss: 37, pp. 669, Mar. 1996.

O'Reilly et al., Angiostatin induces and sustains dormancy of human primary tumors in mice, *Nature Medicine*, Vol/Iss: 2 (6), pp. 689–692, Jun. 1996.

O'Reilly et al., The Suppression of Tumor Metastases by a Primary Tumor, *79th Annual Clinical Congress—San Francisco—Surgical Forum*, Vol/Iss: XLIV, pp. 474–476, 1993.

O'Reilly et al., Angiostatin: A Novel Angiogenesis Inhibitor that Mediates the Suppression of Metastases by a Lewis Lung Carcinoma, *Cell*, Vol/Iss: 79, pp. 315–328, Oct. 21, 1994.

O'Reilly et al., Angiostatin: A Circulating Endothelial Cell Inhibitor That Suppresses Angiogenesis and Tumor Growth, *Cold Spring Habor Symposia on Quantitative Biology*, Vol/Iss: LIX, pp. 471–482, 1994.

Obeso, J. et al., Methods in Laboratory Investigation/A Hemangioendothelioma–Derived Cell Line: Its Use as a Model for the Study of Endothelial Cell Biology, *Laboratory: Investigation*, Vol/Iss: 63 (2), pp. 259–269, 1990.

Osterud, B. et al., Sites of Tissue Factor Pathway Inhibitor (TFPI) and Tissue Factor Expression under Physiologic and Pathologic Conditions, *Thrombosis and Haemostasis*, Vol/Iss: 73, pp. 873–875, 1995.

Parangi, S. et al., Antiangiogenic therapy of transgenic mice impairs de novo tumor growth, *Proceedings of the National Academy of Science USA*, Vol/Iss: 93, pp. 2002–2007, Mar. 1996.

Passaniti, A. et al., Methods in Laboratory Investigation/A Simple, Quantitative Method for Assessing Angiogenesis and Antiangiogenic Agents Using Reconstituted Basement Membrane, Heparin, Fibroblast Growth Factor, *Laboratory: Investigation*, Vol/Iss: 67(4), pp. 519–528, 1992.

Peterson, L.C. et al., Inhibitory Properties of a Novel Human Kunitz–Type Protease Inhibitor Homologous to Tissue Factor Pathway Inhibitor, *Biochemistry*, Vol/Iss: 35, pp. 266–272, Jan. 1, 1996.

Pilgrim et al., Proliferation kultivierter Endotheizellen unter dem Einfluβ von Aprontinin und 4–Aminomethylbezoesaure (no translation), *Biomedica Biochimica Acta*, Vol/Iss: 45 (8), pp. 1015–1019, 1986.

Rao et al., Mechanism of Antithrombin III Inhibition of Factor VIIa/Tissue Factor Activity on Cell Surfaces. Comparison With Tissue Factor Pathway Inhibitor/Factor Xa–Induced Inhibition of Factor VIIa/Tissue Factor Activity, *Blood*, Vol/Iss: 85 (1), pp. 121–129, Jan. 1, 1995.

Rastinejad, F. et al., Regulation of the Activity Of A New Inhibitor Of Angiogenesis By A Cancer Suppressor Gene, *Cell*, Vol/Iss: 56, pp. 345–355, Feb. 10, 1989.

Ridray, S., Hyuperinsulinemia and smooth muscle cell proliferation, *International Journal of Obesity*, Vol/Iss. 19 Supp.l, pp. S39–S51, May, 1995.

Samama, M.M. et al., Mechanisms for the Antithrombotic Activity in Man of Low Molecular Weight Heparins (LMWHs), *Haemostasis*, Vol/Iss: 24, pp. 105–117, Jan. 1, 1994.

Schutte et al., Title: Additional Aspects of the Effect of Kallikrein on Cell Proliferation, *Kinogenases: Kallikrein Symposium Physiol. Prop. Pharmacol.*, Vol/Iss: 4th Edition, pp. 161–177, 1997.

Sprecher, C.A. et al., Molecular cloning, expression, and partial characterization of a second human tissue–factor–pathway inhibitor, *Proceedings of the National Academy of Science USA*, Vol/Iss: 91, pp. 3353–3357, Apr. 1994.

Srigley, J.R., Small–Acinar Patterns in the Prostate Gland With Emphasis on Atypical Adenomatous Hyperplasia and Small–Acinar Carcinoma, *Seminars in Diagnostic Pathology*, Vol/Iss: 5 (3), pp. 254–720, Aug. 1988.

Srivastava, A. et al., The Prognostic Significance of Tumor Vascularity In Intermediate–Thickness (0.76–4.0 mm Thick) Skin Melanoma, *American Journal of Pathology*, Vol/Iss: 133 (2), pp. 419–424, Nov. 1988.

Steinhubl, S.R. et al., Local Delivery of Tissue Factor Pathway Inhibitor (TFPI) to Reduce Neointimal Proliferation in the Porcine Coronary Balloon Injury Model (Abstract only), *Journal of the American College of Cardiology*, Vol/Iss: 29 (2) Supp. A, pp. 97557, Feb. 1997.

Taylor, S. et al., Protamine is an inhibitor of angiogenesis, *Nature*, Vol/Iss: 297, pp. 307–312, May 27, 1982.

Teicher, B.A. et al., Potentiation of Cytotoxic Cancer Therapies by TNP–470 Alone and with Other Antiangiogenic Agents, *International Journal of Cancer*, Vol/Iss: 57 (6), pp. 920–925, 1994.

Voest, E.E. et al., Inhibition of Angiogenesis in Vivo by Interleukin 12, *Journal of the National Cancer Institute*, Vol/Iss: 87, pp. 581–586, Apr. 19, 1995.

Warshawsky, I. et al., The Carboxy Terminus of Tissue Factor Pathway Inhibitor is Required for Interacting with Hepatoma Cells in Vitro and In Vivo, *The American Society for Clinical Investigation*, Vol/Iss: 95, pp. 1773–1782, Apr. 1995.

Warshawsky, I. et al., Title: The low density lipoprotein receptor–related protein mediates the cellular degradation of tissue factor pathway inhibitor, *Proceedings of the National Academy of Science USA*, Vol/Iss: 91, pp. 6664–6668, Jul. 1994.

Weidner, N. et al., Tumor angiogenesis: A New Significant and Independent Prognostic Indicator in Early–Stage Breast Carcinoma, *Journal of the National Cancer Institute*, Vol/Iss: 84, pp. 1875–1887, Dec. 16, 1992.

Weidner, N. et al., Tumor Angiogenesis Correlates with Metastasis in Invasive Prostate Carcinoma, Publ: *American Journal of Pathology*, Vol/Iss: 143 (2), pp. 401–409, Aug. 1993.

Weidner, N. et al., Tumor Angiogenesis and Metastasis–Correlation in Invasive Breast Carcinoma, *New England Journal of Medicine*, Vol/Iss: 324 (1), pp. 1–8, Jan. 3, 1991.

FIGURE 10

SEQ ID NO: 1

| Lys | Gln | Glu | Cys | Leu | Arg | Ala | Cys | Lys | Lys |     |
|-----|-----|-----|-----|-----|-----|-----|-----|-----|-----|-----|
| Gly | Phe | Ile | Gln | Arg | Ile | Ser | Lys | Gly | Gly | Lev | Ile |
| Lys | Thr | Lys | Arg | Lys | Arg | Lys | Lys | Gln | Arg | Val | Lys |
| Ile | Ala | Tyr | Glu | Glu | Ile | Phe | Val | Lys | Asn | Met |     |

SEQ ID NO: 2

| Ile | Ser | Lys | Gly | Gly | Leu | Ile |     |     |     |     |     |
| Lys | Thr | Lys | Arg | Lys | Arg | Lys | Lys | Gln | Arg | Val | Lys |
| Ile | Ala | Tyr | Glu | Glu | Ile | Phe | Val | Lys | Asn | Met |     |

SEQ ID NO: 3

| Lys | Thr | Lys | Arg | Lys | Arg | Lys | Lys | Gln | Arg | Val | Lys |
| Ile | Ala | Tyr | Glu | Glu | Ile | Phe | Val | Lys | Asn | Met |     |

SEQ ID NO: 4

| Lys | Lys | Lys | Lys | Lys | Met | Phe | Lys | Leu | Arg | Phe | Ala |
| Ser | Arg | Ile | Arg | Lys | Ile | Arg | Lys | Lys | Gln | Phe |     |

FIGURE 11

```
Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20              25                  30

Gly Pro Cys Lys Ala Ile Met Lys Arg Phe Phe Phe Asn Ile Phe Thr
        35              40                  45

Arg Gln Cys Glu Glu Phe Ile Tyr Gly Gly Cys Glu Gly Asn Gln Asn
    50              55                  60

Arg Phe Glu Ser Leu Glu Glu Cys Lys Lys Met Cys Thr Arg Asp Asn
65              70              75                      80

Ala Asn Arg Ile Ile Lys Thr Thr Leu Gln Gln Glu Lys Pro Asp Phe
            85                  90                  95

Cys Phe Leu Glu Glu Asp Pro Gly Ile Cys Arg Gly Tyr Ile Thr Arg
            100             105                 110

Tyr Phe Tyr Asn Asn Gln Thr Lys Gln Cys Glu Arg Phe Lys Tyr Gly
        115             120                 125

Gly Cys Leu Gly Asn Met Asn Asn Phe Glu Thr Leu Glu Glu Cys Lys
    130             135                 140

Asn Ile Cys Glu Asp Gly Pro Asn Gly Phe Gln Val Asp Asn Tyr Gly
145             150              155                     160

Thr Gln Leu Asn Ala Val Asn Asn Ser Leu Thr Pro Gln Ser Thr Lys
            165             170                 175

Val Pro Ser Leu Phe Glu Phe His Gly Pro Ser Trp Cys Leu Thr Pro
            180             185                 190

Ala Asp Arg Gly Leu Cys Arg Ala Asn Glu Asn Arg Phe Tyr Tyr Asn
        195             200                 205

Ser Val Ile Gly Lys Cys Arg Pro Phe Lys Tyr Ser Gly Cys Gly Gly
        210             215                 220

Asn Glu Asn Asn Phe Thr Ser Lys Gln Glu Cys Leu Arg Ala Cys Lys
225             230                 235                 240

Lys Gly Phe Ile Gln Arg Ile Ser Lys Gly Gly Leu Ile Lys Thr Lys
            245                 250                 255

Arg Lys Arg Lys Lys Gln Arg Val Lys Ile Ala Tyr Glu Glu Ile Phe
            260                 265                 270
Val Lys Asn Met
            275
```

FIGURE 12

```
Asp Ala Ala Gln Glu Pro Thr Gly Asn Asn Ala Glu Ile Cys Leu Leu
 1            5                    10                    15

Pro Leu Asp Tyr Gly Pro Cys Arg Ala Leu Leu Leu Arg Tyr Tyr Tyr
             20                  25                30

Asp Arg Tyr Thr Gln Ser Cys Arg Gln Phe Leu Tyr Gly Gly Cys Glu
         35                  40                45

Gly Asn Ala Asn Asn Phe Tyr Thr Trp Glu Ala Cys Asp Asp Ala Cys
     50              55                  60

Trp Arg Ile Glu Lys Val Pro Lys Val Cys Arg Leu Gln Val Ser Val
 65              70                  75                    80

Asp Asp Gln Cys Glu Gly Ser Thr Glu Lys Tyr Phe Phe Asn Leu Ser
                 85                  90                    95

Ser Met Thr Cys Glu Lys Phe Phe Ser Gly Gly Cys His Arg Asn Arg
            100                 105                 110

Ile Glu Asn Arg Phe Pro Asp Glu Ala Thr Cys Met Gly Phe Cys Ala
        115                 120                 125

Pro Lys Lys Ile Pro Ser Phe Cys Tyr Ser Pro Lys Asp Glu Gly Leu
    130             135                 140
145

Cys Ser Ala Asn Val Thr Arg Tyr Tyr Phe Asn Pro Arg Tyr Arg Thr
145                 150                 155                 160

Cys Asp Ala Phe Thr Tyr Thr Gly Cys Gly Gly Asn Asp Asn Asn Phe
                165                 170                 175

Val Ser Arg Glu Asp Cys Lys Arg Ala Cys Ala Lys Ala Leu Lys Lys
            180                 185                 190

Lys Lys Lys Met Pro Lys Leu Arg Phe Ala Ser Arg Ile Arg Lys Ile
        195                 200                 205

Arg Lys Lys Gln Phe
    210
```

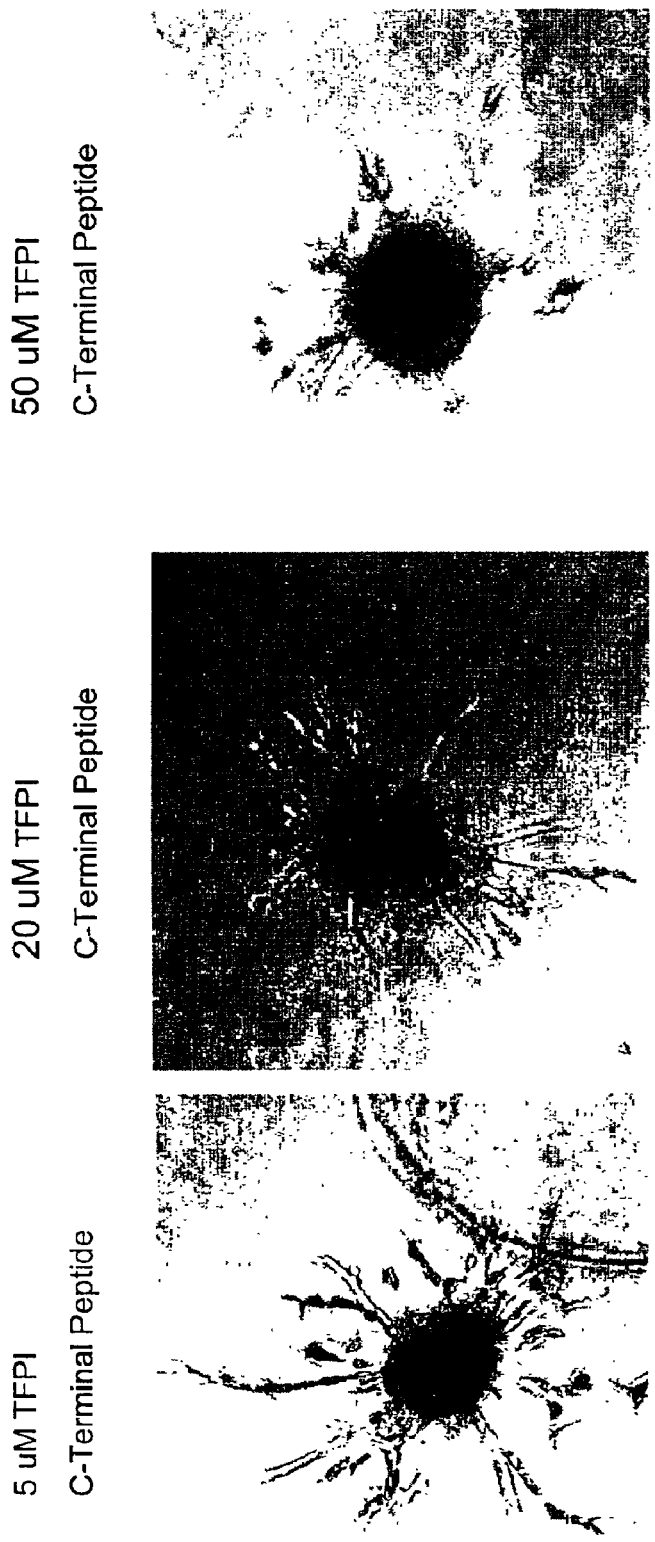
Figure 13 (a-c)

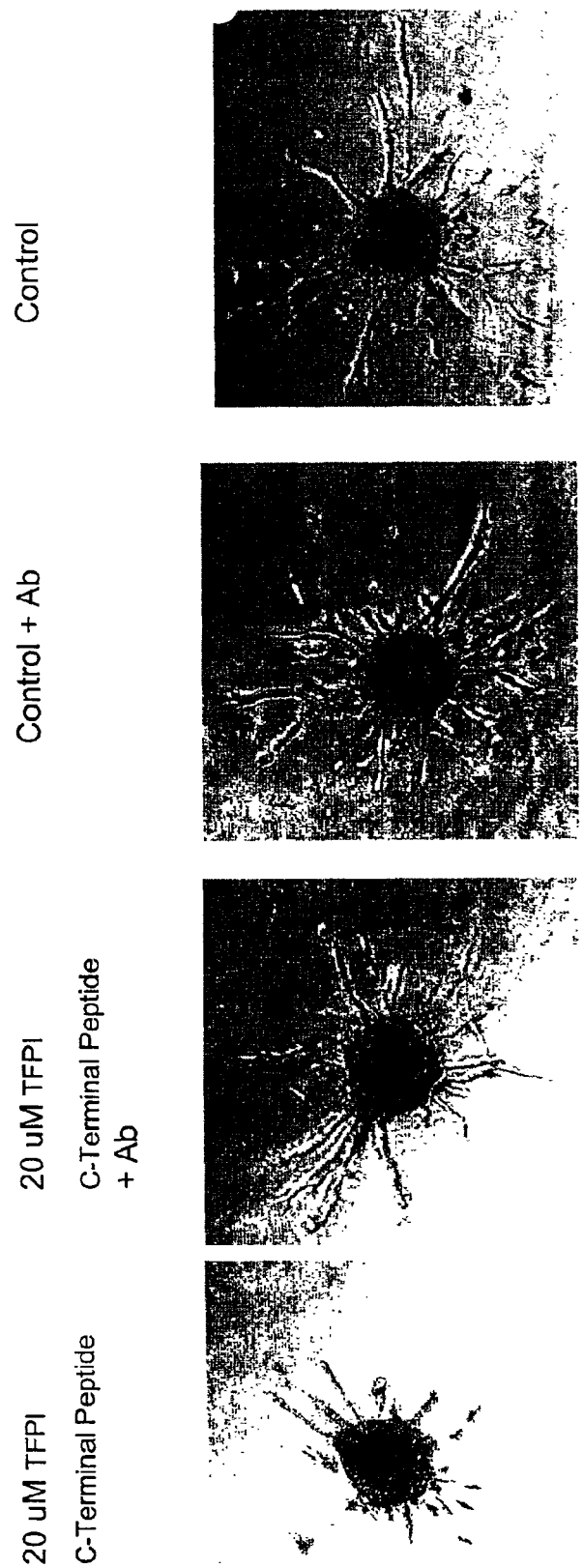
Figure 14 (a-d)

US 6,946,439 B2

COMPOSITIONS AND METHODS FOR INHIBITING CELLULAR PROLIFERATION COMPRISING TFPI FRAGMENTS

CROSS-REFERENCE TO RELATED APPLICATIONS

This is a continuation-in-part application of U.S. patent application Ser. No. 09/766,778 filed Jan. 22, 2001 now U.S. Pat. No. 6,734,163, which is a continuation application of U.S. patent application Ser. No. 09/227,955 filed Jan. 11, 1999 (now abandoned) which is a continuation of U.S. patent application Ser. No. 08/796,850 filed Feb. 6, 1997 now U.S. Pat. No. 5,981,471 issued Nov. 9, 1999. This is also a continuation-in-part application of U.S. patent application Ser. No. 09/130,273 filed Aug. 6, 1998 now abandoned which is a continuation-in-part of U.S. patent application Ser. No. 08/796,850 filed Feb. 6, 1997 now U.S. Pat. No. 5,981,471 issued Nov. 9, 1999.

FIELD OF THE INVENTION

The present invention relates to methods and compositions for the inhibition of cellular proliferation. More particularly, the present invention relates to the use of tissue factor pathway inhibitor proteins or peptides, and active fragments thereof, for inhibiting angiogenesis and angiogenesis-related diseases.

BACKGROUND OF THE INVENTION

Cellular proliferation is a normal ongoing process in all living organisms and is one that involves numerous factors and signals that are delicately balanced to maintain regular cellular cycles. The general process of cell division is one that consists of two sequential processes: nuclear division (mitosis), and cytoplasmic division (cytokinesis). Because organisms are continually growing and replacing cells, cellular proliferation is a central process that is vital to the normal functioning of almost all biological processes. Whether or not mammalian cells will grow and divide is determined by a variety of feedback control mechanisms, which include the availability of space in which a cell can grow, and the secretion of specific stimulatory and inhibitory factors in the immediate environment.

When normal cellular proliferation is disturbed or somehow disrupted, the results can affect an array of biological functions. Disruption of proliferation could be due to a myriad of factors such as the absence or overabundance of various signaling chemicals or presence of altered environments. Some disorders characterized by abnormal cellular proliferation include cancer, abnormal development of embryos, improper formation of the corpus luteum, difficulty in wound healing as well as malfunctioning of inflammatory and immune responses.

Cancer is characterized by abnormal cellular proliferation. Cancer cells exhibit a number of properties that make them dangerous to the host, often including an ability to invade other tissues and to induce capillary ingrowth, which assures that the proliferating cancer cells have an adequate supply of blood. One of the defining features of cancer cells is that they respond abnormally to control mechanisms that regulate the division of normal cells and continue to divide in a relatively uncontrolled fashion until they kill the host.

Angiogenesis and angiogenesis related diseases are closely affected by cellular proliferation. As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" is defined herein as a thin layer of flat cells that lines serous cavities, lymph vessels, and blood vessels. These cells are defined herein as "endothelial cells". The term "endothelial inhibiting activity" means the capability of a molecule to inhibit angiogenesis in general. The inhibition of endothelial cell proliferation also results in an inhibition of angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic-dependent, angiogenic-associated, or angiogenic-related diseases. These diseases are a result of abnormal or undesirable cell proliferation, particularly endothelial cell proliferation.

The hypothesis that tumor growth is angiogenesis-dependent was first proposed in 1971 by Judah Folkman (N. Engl. Jour. Med. 285:1182 1186, 1971). In its simplest terms the hypothesis proposes that once tumor "take" has occurred, every increase in tumor cell population must be preceded by an increase in new capillaries converging on the tumor. Tumor "take" is currently understood to indicate a prevascular phase of tumor growth in which a population of tumor cells occupying a few cubic millimeters volume and not exceeding a few million cells, survives on existing host microvessels. Expansion of tumor volume beyond this phase requires the induction of new capillary blood vessels. For example, pulmonary micrometastases in the early prevascular phase in mice would be undetectable except by high power microscopy on histological sections. Further indirect evidence supporting the concept that tumor growth is angiogenesis dependent is found in U.S. Pat. No. 5,885,795 which is incorporated herein by reference.

Thus, it is clear that cellular proliferation, particularly endothelial cell proliferation, and most particularly angiogenesis, plays a major role in the metastasis of a cancer. If this abnormal or undesirable proliferation activity could be repressed, inhibited, or eliminated, then the tumor, although present, would not grow. In the disease state, prevention of abnormal or undesirable cellular proliferation and angiogenesis could avert the damage caused by the invasion of the new microvascular system. Therapies directed at control of the cellular proliferative processes could lead to the abrogation or mitigation of these diseases.

What are needed therefore, are methods and compositions that can inhibit abnormal or undesirable cellular proliferation, especially the growth of blood vessels into tumors. Such methods and compositions should be able to overcome the activity of endogenous growth factors in premetastatic tumors and prevent the formation of capillaries in the tumors thereby inhibiting the development of disease and the growth of tumors. Such methods and compositions should also be able to modulate the formation of capillaries in angiogenic processes, such as wound healing and reproduction. Finally, the methods and compositions for inhibiting cellular proliferation should preferably be non-toxic and produce few side effects.

SUMMARY OF THE INVENTION

Methods and compositions are provided that are effective in inhibiting abnormal or undesirable cell proliferation, particularly endothelial cell proliferation and angiogenesis related to neovascularization and tumor growth. The compositions of the present invention comprise a naturally occurring or synthetic protein, peptide, or protein fragment containing all, or an active portion of proteinase inhibitors such as tissue factor pathway inhibitor (TFPI), optionally combined with a pharmaceutically acceptable carrier. Preferably, the protein, peptide or protein fragment contains all or an active portion of the carboxyl terminal of TFPI. The term "active portion", as used herein, means a portion of a protein that inhibits abnormal or undesirable cell proliferation.

As used herein, the term TFPI includes, but is not limited to, tissue factor pathway inhibitor I (TFPI), tissue factor pathway inhibitor II (TFPI-2), and active portions thereof. Also included are TFPI homologs, peptides of TFPI or TFPI-2 homologs, and protein fragments of TFPI or TFPI-2 homologs. Preferably, the protein, peptide, or protein fragment is a protein, peptide or protein fragment of TFPI or a TFPI-2 homolog containing the carboxyl terminal or an active portion thereof. Most preferably, the protein, peptide, or protein fragment of the present invention is a protein, peptide or protein fragment of TFPI or a TFPI-2 homolog comprising or corresponding to the carboxyl terminal amino acids of the primary sequence of TFPI within the range of the final 45 amino acids (SEQ ID NO: 1) and is further characterized in its ability to bind with the very low density lipoprotein (VLDL) receptor. In a more preferred embodiment the protein or peptide comprises the final 30 amino acids of the TFPI carboxyl terminal protein (SEQ ID NO: 2). The most preferred embodiment of the present invention comprises a peptide corresponding to the 23 amino acids that comprise the carboxyl terminal of the primary sequence of TFPI and is set forth below as SEQ ID NO: 3.

Lys Thr Lys Arg Lys Arg Lys Lys Gln Arg Val Lys Ile Ala Tyr Glu Glu Ile Phe Val Lys Asn Met (SEQ ID NO: 3)

In an alternatively preferred embodiment, the present invention comprises a peptide corresponding to the final 23 amino acids that comprise the carboxyl terminal of the primary sequence of TFPI-2 as set forth below as SEQ ID NO: 4

Lys Lys Lys Lys Lys Met Phe Lys Leu Arg Phe Ala Ser Arg Ile Arg Lys Ile Arg Lys Lys Gln Phe (SEQ ID NO: 4)

It is believed that by inhibiting endothelial cell proliferation, the compositions described herein are useful for inhibiting tumor growth and metastasis by blocking tumor vascularization.

The methods provided herein for treating diseases and processes mediated by undesired and uncontrolled cell proliferation, such as cancer, involve administering to a human or animal the compositions described herein in a dosage sufficient to inhibit cell proliferation, particularly endothelial cell proliferation. The method is especially useful for treating or repressing the growth of tumors, particularly by inhibiting angiogenesis. Administration of the compositions to a human or animal having prevascularized metastasized tumors is useful for preventing the growth or expansion of such tumors.

Accordingly, it is an object of the present invention to provide methods of treating diseases and processes that are mediated by abnormal or undesirable cellular proliferation.

It is another object of the present invention to provide compositions for treating or repressing the growth of a cancer.

It is yet another object of the present invention to provide a therapy for cancer that has minimal side effects.

It is another object of the present invention to provide methods and compositions for treating diseases and processes that are mediated by angiogenesis.

These and other objects, features and advantages of the present invention will become apparent after a review of the following detailed description of the disclosed embodiments and the appended claims.

BRIEF DESCRIPTION OF THE FIGURES

FIG. 10 provides amino acid sequences for peptides comprising the carboxyl terminal of TFPI: the terminal 45 amino acids (SEQ ID NO: 1), the terminal 30 amino acids (SEQ ID NO: 2), the terminal 23 amino acids (SEQ ID NO: 3), and the terminal 23 amino acids from TFPI-2 (SEQ ID NO: 4).

FIG. 11 is the amino acid sequence of tissue factor pathway inhibitor (TFPI) (SEQ ID NO: 5).

FIG. 12 is the amino acid sequence of tissue factor pathway inhibitor-2 (TFPI-2) (SEQ ID NO: 6).

FIG. 13(a-c) provides schematics demonstrating that increasing amounts of C-terminal peptide inhibit the sprouting of vessel-like structures on spheroids: (a) 5 µM, (b) 20 µM, and (c) 50 µM.

FIG. 14(a-d) provides schematics demonstrating the effect of the C-terminal peptide in the presence and absence of a VLDL antibody: (a) 20 µM TFPI C-terminal peptide, (b) 20 µM TFPI C-terminal peptide plus VLDL antibody, (c) control plus VLDL antibody, and (d) control.

DETAILED DESCRIPTION

Figure 1:
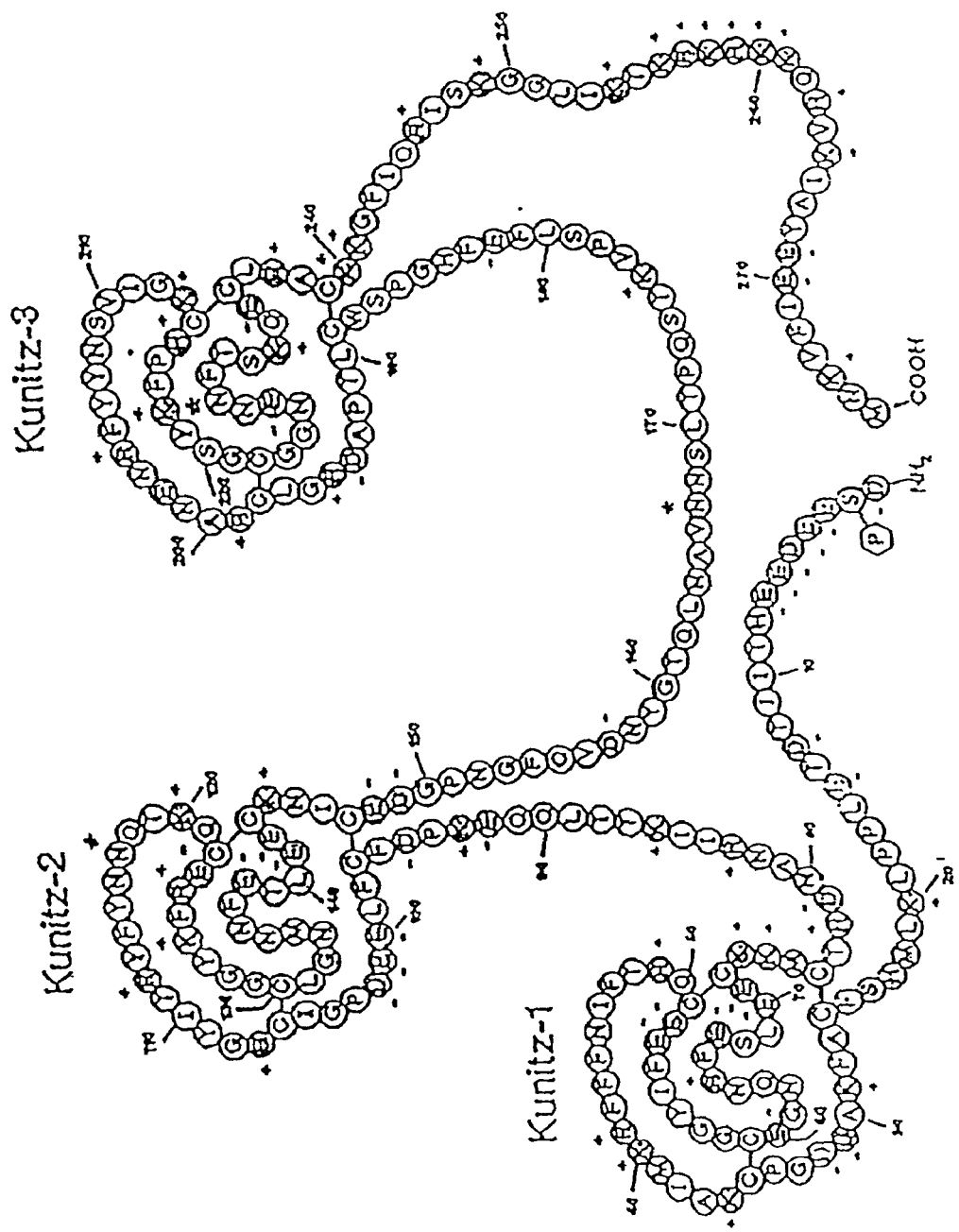
FIG. 1 is a schematic diagram of tissue factor pathway inhibitor (TFPI) showing its structure.
Figure 2:
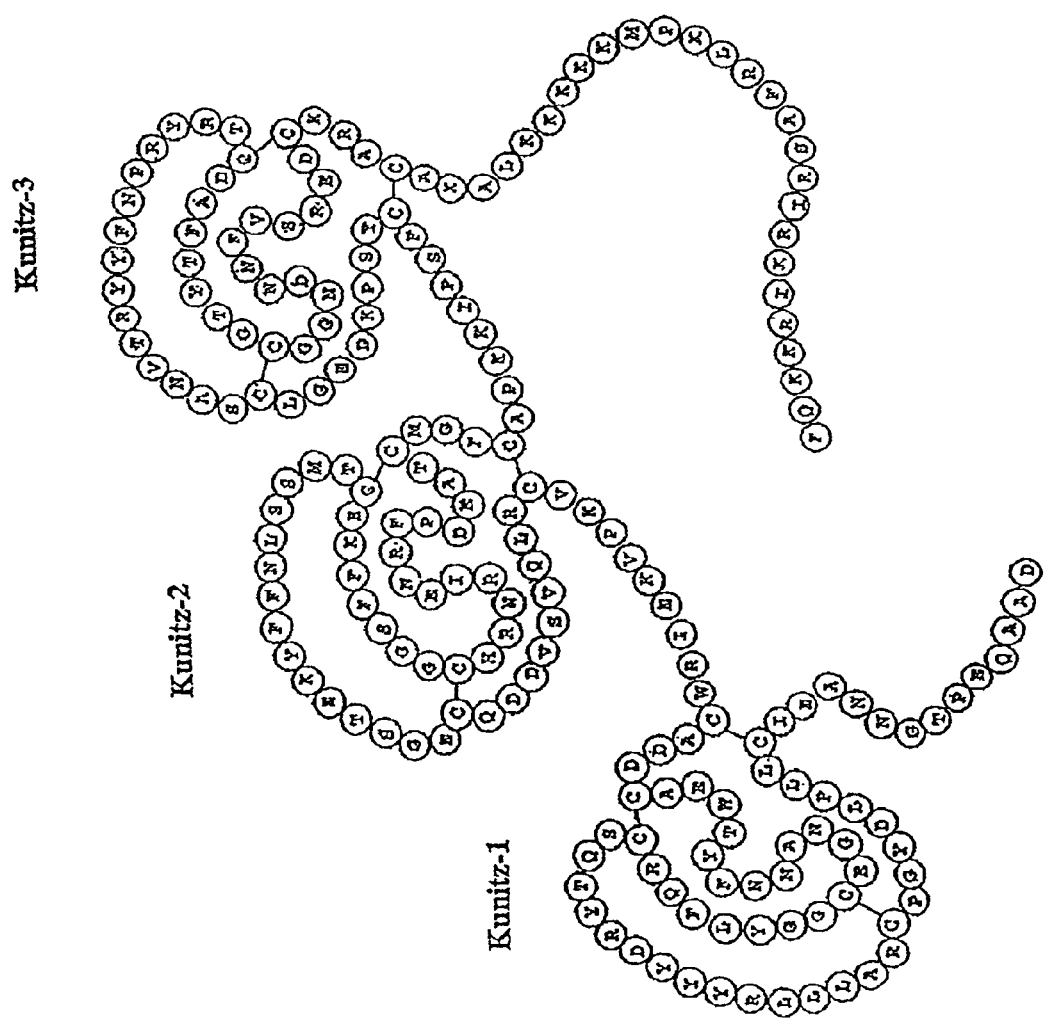
FIG. 2 is a schematic diagram of tissue factor pathway inhibitor-2 (TFPI-2) showing its structure.
Figure 3:
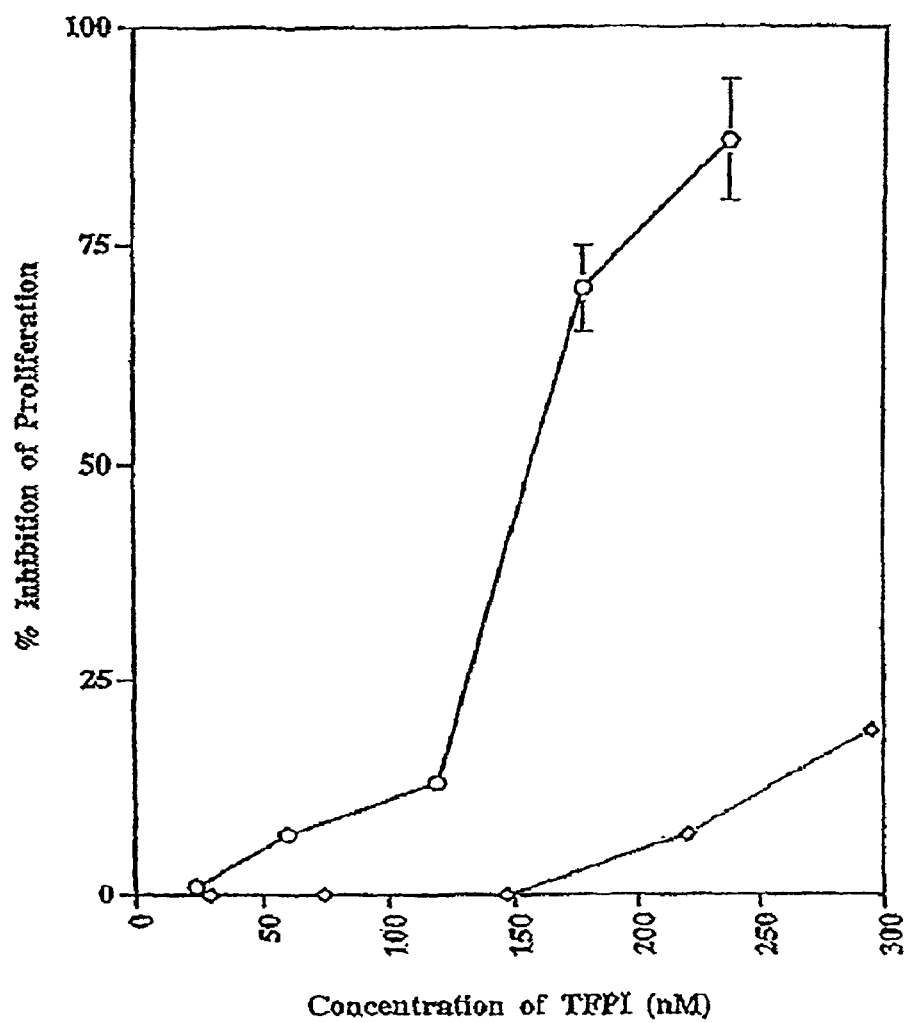
FIG. 3 is a graph showing the antiproliferative activity of recombinant human full length TFPI (open circle) and truncated TFPI (open diamond) in the presence of 10 ng/ml bFGF. Each point represents the average of three wells and is a representative of four experiments. Error bars represent standard deviation.
Figure 4:
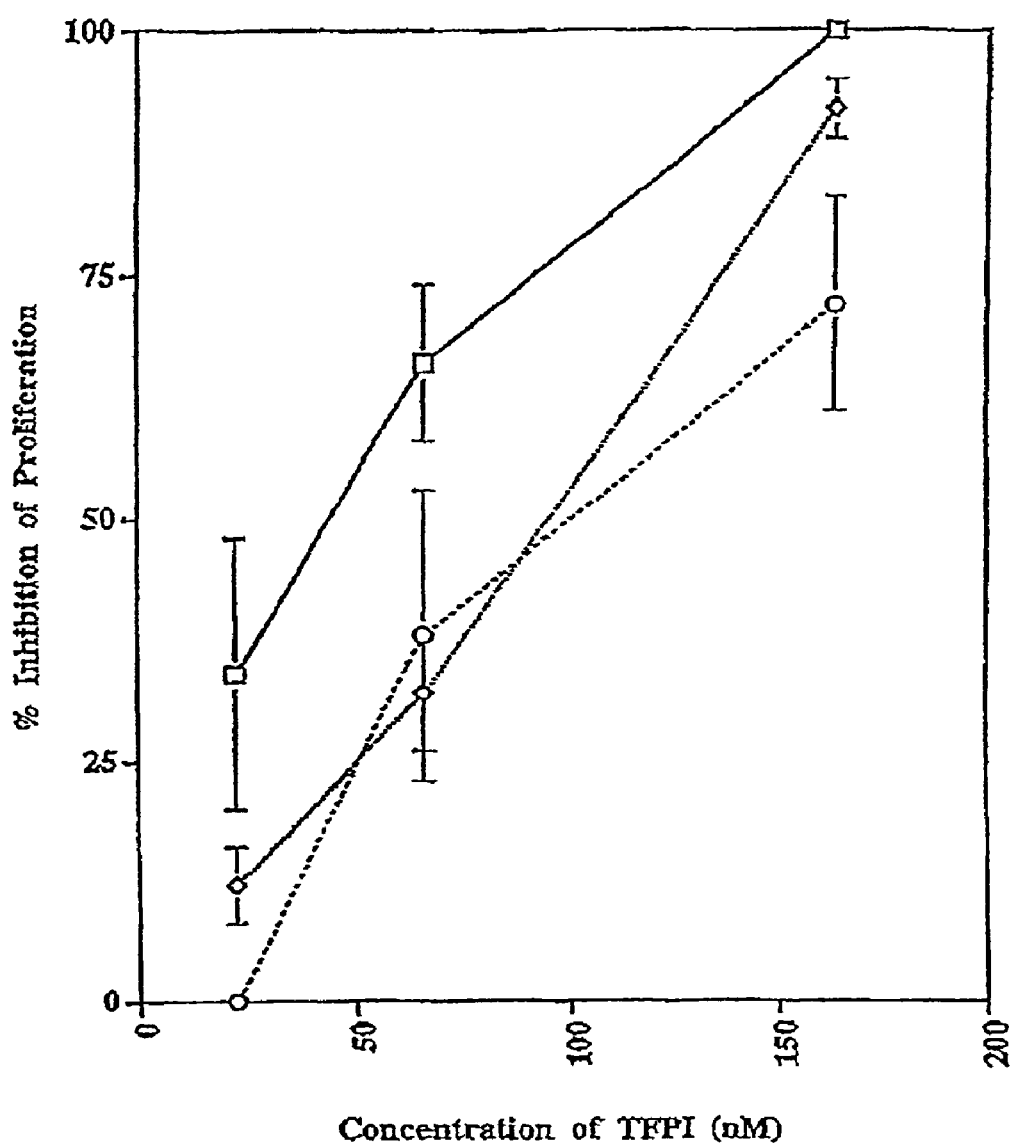
FIG. 4 is a dose response graph showing cell proliferation activity after administration of TFPI in the presence of various amounts of bFGF: 0.5 ng/ml bFGF (open square), 1.0 ng/ml bFGF (open diamond), 5.0 ng/ml bFGF (open circle). Each point represents the average of three wells and is a representative of four experiments. Error bars represent standard deviation.

The following description includes the best presently contemplated mode of carrying out the invention. This description is made for the purpose of illustrating the general principles of the inventions and should not be taken in a limiting sense. All publications, references, applications and patents listed or cited herein are incorporated by reference in their entirety.

Compositions and methods for the treatment of diseases and processes that are mediated by, or associated with, abnormal or undesirable cellular proliferation are provided.

The compositions of the present invention generally comprise proteinase inhibitors and peptides having antiproliferative, namely antiangiogenic activity. More specifically, the compositions comprise isolated naturally occurring or synthetic protein, peptide, or protein fragments, containing all or an active portion of a "tissue factor pathway inhibitor" (TFPI) protein. For delivery to a human or animal, the compositions may further optionally comprise a pharmaceutically acceptable carrier. The term "active portion" is defined herein as a portion of a protein that inhibits abnormal or undesirable cell proliferation. The active portion has the ability to inhibit endothelial cell proliferation as demonstrated and assessed in in vivo or in vitro assays or other known techniques. Preferably, the compositions comprise the carboxyl terminal end of TFPI, or a peptide or fragment thereof. More preferably, the protein, peptide, or protein fragment is a protein, peptide or protein fragment of TFPI containing or corresponding to the final 45 amino acids of the TFPI carboxyl terminal end. Most preferably the compositions of the present invention comprise proteins or peptides containing or corresponding to the final 30 amino acids of the TFPI carboxyl terminal end, and in a most preferred embodiment the compositions of the present invention comprise proteins or peptides containing or corresponding to the final 23 amino acids of the TFPI carboxyl terminal end and active portions thereof having antiproliferative activity as described below. The amino acid sequences of the above-described peptides from the TFPI carboxyl terminal end are set forth in FIG. 10 as SEQ ID NOS: 1–3.

In an alternatively preferred embodiment, the present invention comprises compositions comprising peptides having the terminal 23 amino acids of TFPI-2. The preferred amino acid sequence of such peptides is set forth in FIG. 10 as SEQ ID NO: 4.

In accordance with the methods, the compositions described herein, containing a protein, peptide, or protein fragment including all or an active portion of one or more TFPI proteins, optionally combined with a pharmaceutically acceptable carrier, are administered to humans or animals exhibiting undesirable cellular proliferation in an amount sufficient to inhibit the undesirable cell proliferation, particularly endothelial cell proliferation, angiogenesis or an angiogenesis-related disease, such as cancer.

Definitions

The terms "a", "an" and "the" as used herein are defined to mean one or more and include the plural unless the context is inappropriate.

The term "peptides," are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" is used herein to refer to an amino acid that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The phrase "consisting essentially of" is used herein to exclude any elements that would substantially alter the essential properties of the peptides to which the phrase refers. Thus, the description of a peptide "consisting essentially of . . . " excludes any amino acid substitutions, additions, or deletions that would substantially alter the biological activity of that peptide.

Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);

4) Arginine (R), Lysine (K);
5) Isoleucine (I), Leucine (L), Methionine (M), Valine (V); and
6) Phenylalanine (F), Tyrosine (Y), Tryptophan (W).

The phrases "isolated" or "biologically pure" refer to material which is substantially or essentially free from components which normally accompany it as found in its native state. Thus, the peptides described herein do not contain materials normally associated with their in situ environment. Typically, the isolated, antiproliferative peptides described herein are at least about 80% pure, usually at least about 90%, and preferably at least about 95% as measured by band intensity on a silver stained gel.

Protein purity or homogeneity may be indicated by a number of methods well known in the art, such as polyacrylamide gel electrophoresis of a protein sample, followed by visualization upon staining. For certain purposes high resolution will be needed and HPLC or a similar means for purification utilized.

The term "residue" refers to an amino acid (D or L) or an amino acid mimetic incorporated in a oligopeptide by an amide bond or amide bond mimetic. An amide bond mimetic includes peptide backbone modifications well known to those skilled in the art.

When the antiproliferative peptides are relatively short in length (i.e., less than about 50 amino acids), they are often synthesized using standard chemical peptide synthesis techniques.

Solid phase synthesis in which the C-terminal amino acid of the sequence is attached to an insoluble support followed by sequential addition of the remaining amino acids in the sequence is a preferred method for the chemical synthesis of the antiproliferative peptides described herein. Techniques for solid phase synthesis are known to those skilled in the art.

Alternatively, the antiproliferative peptides described herein are synthesized using recombinant nucleic acid methodology. Generally, this involves creating a nucleic acid sequence that encodes the peptide, placing the nucleic acid in an expression cassette under the control of a particular promoter, expressing the peptide in a host, isolating the expressed peptide or polypeptide and, if required, renaturing the peptide. Techniques sufficient to guide one of skill through such procedures are found in the literature.

Once expressed, recombinant peptides can be purified according to standard procedures, including ammonium sulfate precipitation, affinity columns, column chromatography, gel electrophoresis and the like. Substantially pure compositions of about 50 to 95% homogeneity are preferred, and 80 to 95% or greater homogeneity are most preferred for use as therapeutic agents.

One of skill in the art will recognize that after chemical synthesis, biological expression or purification, the antiproliferative peptides may possess a conformation substantially different than the native conformations of the constituent peptides. In this case, it is often necessary to denature and reduce the antiproliferative peptide and then to cause the peptide to re-fold into the preferred conformation. Methods of reducing and denaturing proteins and inducing refolding are well known to those of skill in the art.

As discussed above, one of skill in the art will recognize that, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid.

Conservative substitution tables providing functionally similar amino acids are well known in the art. Accordingly, also included in the present invention are peptides having conservatively modified variations in comparison to the claimed peptides, wherein the chemical reactivity of the peptide is not significantly different from that of the claimed peptide.

Antiproliferative Proteinase Inhibitors

As mentioned above, the compositions described herein are proteins, peptides or protein fragments of proteinase inhibitors. Most preferably, the protein is TFPI, a TFPI homolog, such as, but not limited to, TFPI-1, TFPI-2, or a protein belonging to a family, or superfamily, of proteins that contain proteinase inhibitor domains, such as, but not limited to, amyloid protein precursor (APP); amyloid beta precursor protein and other serine protease inhibitors; collagen VI; and bovine pancreatic trypsin inhibitor (BPTI).

TFPI is a glycoprotein having a molecular weight of approximately 32 to 45 kilodaltons. TFPI is composed of approximately 276 amino acids organized in a structure that includes an acidic amino terminus followed by three Kunitz-type proteinase inhibitor domains, referred to as Kunitz-1, Kunitz-2, and Kunitz-3, and a basic carboxyl terminal region as shown in FIG. 1. TFPI has a total of three glycosylation sites, located at amino acids 117, 167, and 228. The amino acid sequence of TFPI is set forth in SEQ ID NO: 5.

TFPI, also known to those skilled in the art as lipoprotein-associated coagulation inhibitor (LACI), is a protease inhibitor that plays an important role in the regulation of tissue factor-induced blood coagulation. TFPI functions primarily by interfering with the function of certain components in the blood coagulation system, more specifically by binding and inactivating factor Xa, and binding to and inhibiting Tissue Factor/VIIa.

In the blood coagulation cascade, TFPI blocks the initial steps of the extrinsic pathway by binding and inactivating factor Xa and by binding and inhibiting tissue factor/factor VIIa complex. The Kunitz-1 domain of TFPI is responsible for the inhibition of factor VIIa of the tissue factor/factor VIIa complex while the Kunitz-2 domain is responsible for the inhibition of factor Xa. The role of Kunitz-3 in the blood coagulation cascade is not yet understood, although a heparin-binding site has been localized in its basic region. The main heparin-binding site of TFPI is located in the carboxyl terminus of the molecule.

Generally, TFPI is found in plasma, in platelets, and on endothelium. The plasma concentration of TFPI is low (approximately 3 nM), and the majority of circulating TFPI is bound to lipoproteins (LDL, HDL, and lipoprotein (a)). Platelets carry approximately 10% of the total TFPI concentration, and release it after acute stimulation. At a site of blood vessel injury and after the bleeding has stopped, the concentration of TFPI is three times higher than the normal levels found in plasma. This additional TFPI is derived by the aggregated platelets at the site of the injury. The majority of intravascular TFPI is endothelium-bound and is released after heparin infusion. The amount of the heparin-releasable TFPI is believed to be two to ten times the amount found in plasma or 220–800 ng/ml.

Intravascular TFPI exists in several forms, which are known to those skilled in the art. The predominant forms of plasma TFPI have molecular weights of 34 and 41 KDa but other forms with higher molecular weights are also present. The form of TFPI that circulates while bound to LDL has a molecular mass of 34 KDa and lacks the carboxyl-terminal region and part of the Kunitz-3 domain. The 41 KDa form of TFPI circulates while bound to HDL and is truncated like one of the 34 KDa forms. This form of TFPI has a higher molecular weight because it is linked via a disulfide bond to apolipoprotein A-II. The heparin-releasable TFPI is not truncated and is fully glycosylated.

TFPI is synthesized in endothelial cells and is exocytosed toward the surface of the cells where it remains bound to heparin sulfate proteoglycans (HSPGs). The liver is mainly responsible for the clearance of circulating TFPI. In the liver, the low density lipoprotein receptor-related protein (LRP) mediates the uptake and degradation of TFPI by hepatocyte cells. This LRP-mediated clearance of TFPI involves two steps. Initially TFPI binds to HSPGs on the surface of the cells and is then transferred to LRP for internalization.

TFPI is isolated from body fluids including, but not limited to, serum, urine, and ascites, or is synthesized by chemical or biological methods, such as cell culture, recombinant gene expression, and peptide synthesis. Recombinant techniques include gene amplification from DNA sources using the polymerase chain reaction (PCR), and gene amplification from RNA sources using reverse transcriptase/PCR. The amino acid sequence of TFPI is known and is set forth schematically in FIG. 1 and SEQ ID NO: 5. Peptides and protein fragments of TFPI preferably have an amino acid sequence within the amino acid sequence set forth in SEQ ID NO: 5. TFPI is extracted from body fluids by known protein extraction methods, particularly the method described by Novotny, W. F., et al, *J Biol. Chem.* 264:18832–18837 (1989).

As reported in the Examples below, it was unexpectedly discovered that the TFPI peptide consisting of the carboxyl terminal portion of TFPI and previously unassociated with endothelial cell proliferation, has antiproliferative effects on endothelial cells. Furthermore, as also demonstrated in the Examples, this TFPI peptide was discovered to be a potent inhibitor of tumor growth. The preferred peptide from the carboxyl terminal comprises the final 45 amino acid sequences of TFPI (SEQ ID NO: 1), a more preferred peptide comprises the final 30 amino acid sequences (SEQ ID NO: 2) and the most preferred peptide comprises the final 23 amino acid sequences (SEQ ID NO: 3).

TFPI-2 is a homolog of TFPI and has a molecular mass of 32 kDa. The amino acid sequence of TFPI-2 is set forth in SEQ ID NO: 6. Peptides and fragments of TFPI-2 preferably have an amino acid sequence within the amino acid sequence set forth in SEQ ID NO: 6. Characteristics of TFPI-2 are described in the scientific article of Sprecher, Cindy A., et al., *Proc. Natl. Acad. Sci., USA*, 91:3353–3357 (1994), TFPI-2 is also known by those skilled in the art as placental protein 5 as described in the scientific article of Miyagi, Y., et al., *J. Biochem.* 116:939–942 (1994). Additional properties of TFPI-2 are described in the scientific article of Petersen, L. C., et al., *Biochem.* 35:266–272 (1996).

In an additionally preferred embodiment of the present invention, the methods comprise use of compositions comprising active portions of the carboxyl terminal of TFPI-2. One such peptide comprises the amino acid sequence set forth in SEQ ID NO. 4.

Characterization of TFPI Carboxyl Terminal Peptide

The present invention is directed to proteinase inhibitors and in particular TFPI. As described in U.S. Pat. No. 5,981,471 and U.S. patent application Ser. Nos. 09/766,778 and 09/130,273, we have previously demonstrated that TFPI is a potent inhibitor of endothelial cell proliferation. In light of this data, we sought to identify the specific domains and peptides of TFPI that were responsible for this activity. The initial experiments described below (Example 1) were designed to assess the antiproliferative activity of a peptide consisting of the carboxyl terminal 23 amino acids of TFPI. This peptide is highly basic, and was previously identified as an important domain, which might mediate the cell surface interactions, as well as the antiproliferative activity of TFPI (Hanada et al., *Thrombosis and Haemostasis* (Supplement) p. 2127 (2001)).

Although Hanada et al. reported that the C-terminal peptide of the present invention was effective in inhibiting the proliferation of smooth muscle cells, one skilled in the art would not assume that the effects of a certain agent on smooth muscle cells would have the same or similar effect on endothelial cells. Indeed there are numerous examples of agents having opposite effects on both types of cells, see for example Ridray S., *Int. J. Metab. Disord* 19: S39–51 (1995) (insulin stimulates the proliferation of smooth muscle cells) and Nakao-Hayashi, J. et al. *Atherosclerosis* 92:141–149 (1992) (insulin has no effect on the proliferation of endothelial cells); see also Devaraj S. et al. *Curr. Opin. Lipidol.* 9:11–5 (1998) (alpha tocopherol inhibits proliferation of smooth muscle cells) and Kuzuya et al. *Artery* 18:115–120 (1991) (alpha tocopherol stimulates proliferation of endothelial cells).

Figure 5:
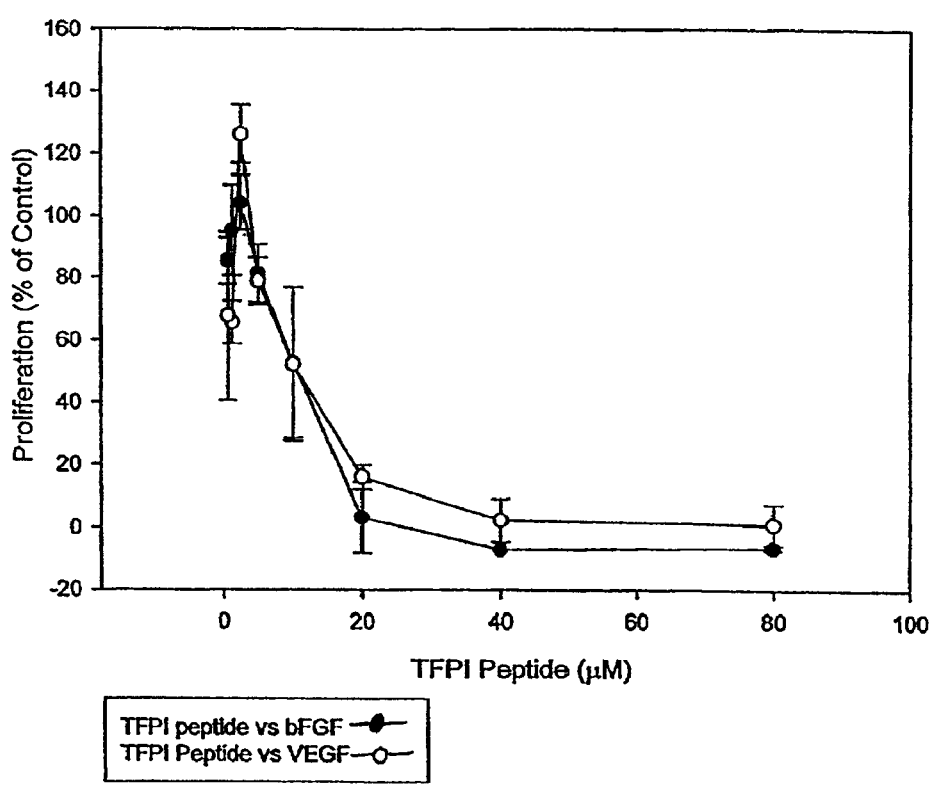
FIG. 5 is a dose response graph showing cell proliferation activity after administration of the TFPI C-terminal peptide in the presence of bFGF (closed circle) and VEGF (open circle).
Figure 6:
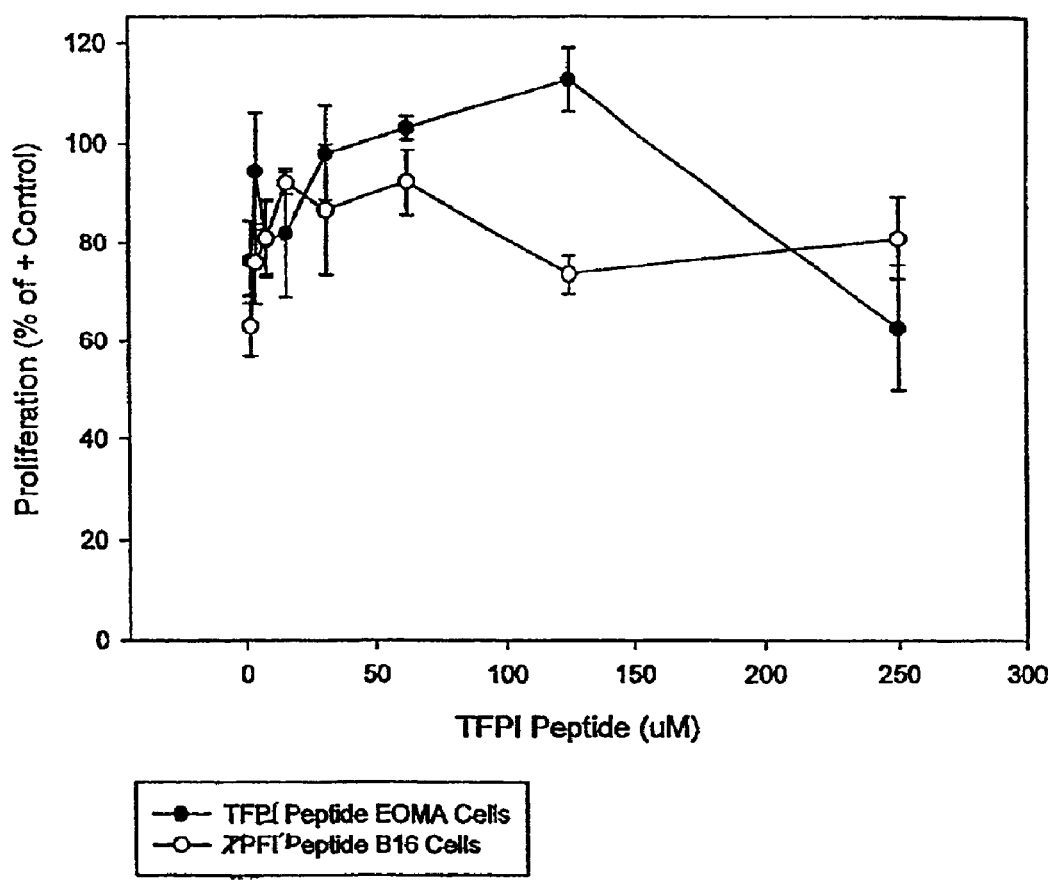
FIG. 6 is a dose response graph showing lack of inhibition of tumor cell proliferation in the presence of varying amounts of the TFPI C-terminal peptide. Closed circles represent the EOMA cell line and the open circles represent the B16 cell line.

The TFPI C-terminal peptide of the present invention was used to treat quiescent HUVECs that had been stimulated with either bFGF or VEGF and as shown in FIG. 5, it was shown to be a potent inhibitor of HUVEC proliferation. Complete inhibition was seen at doses above 20 $\mu$M, and the IC$_{50}$ for this peptide in both assays was around 5 $\mu$M. In contrast, even at doses up to 250 $\mu$M, this peptide did not inhibit the growth of two different tumor cell lines, B16 murine melanoma and EOMA hemangioendothelioma cells (FIG. 6). Though not wishing to be bound by the following theory, it is believed that these studies (together with the tumor inhibition studies described below) demonstrate that inhibition of tumor growth in the presence of the TFPI C-terminal fragment is attributed to the inhibition of endothelial cell proliferation, namely antiangiogenic effect of the TFPI peptide, and not to the inhibition of tumor cell proliferation directly. Control experiments were performed with a scrambled peptide. In these experiments, no inhibition of cell proliferation was seen (data not shown).

Figure 7:
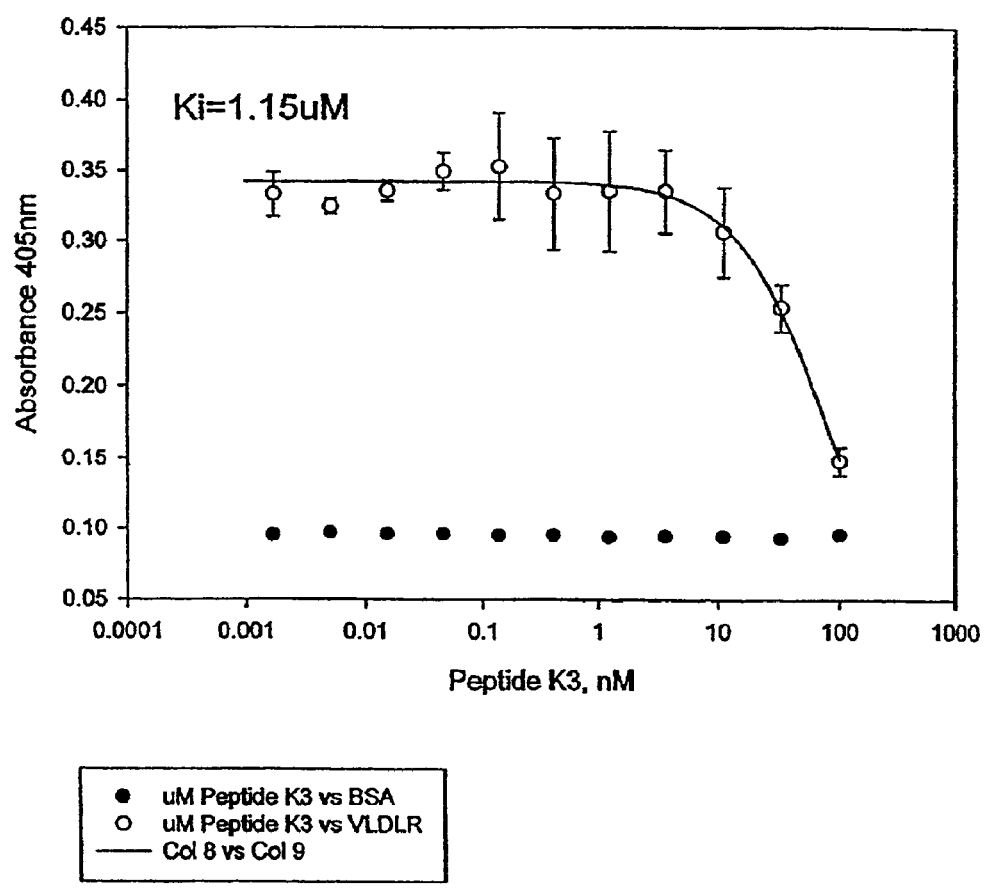
FIG. 7 is a dose response graph showing the inhibition of RAP binding to immobilized sVLDLr1-8 in the presence of the TFPI C-terminal peptide.

We had previously shown that TFPI was a ligand for the VLDL receptor, and that this interaction was necessary for the antiproliferative activity of TFPI (U.S. patent application Ser. No. 09/270,982 filed Mar. 17, 1999). For this reason further experiments were conducted to determine if the TFPI C-terminal peptide was a ligand for the VLDL receptor (Example 2). FIG. 7 demonstrates the results of a competition experiment wherein increasing concentrations of C-terminal peptide were used to block the binding of RAP to immobilized VLDL receptor ligand binding repeats 1–8. As shown in FIG. 7 the TFPI C-terminal peptide blocked binding of RAP to the VLDL receptor demonstrating that the peptide does bind the VLDL receptor.

Figure 8:
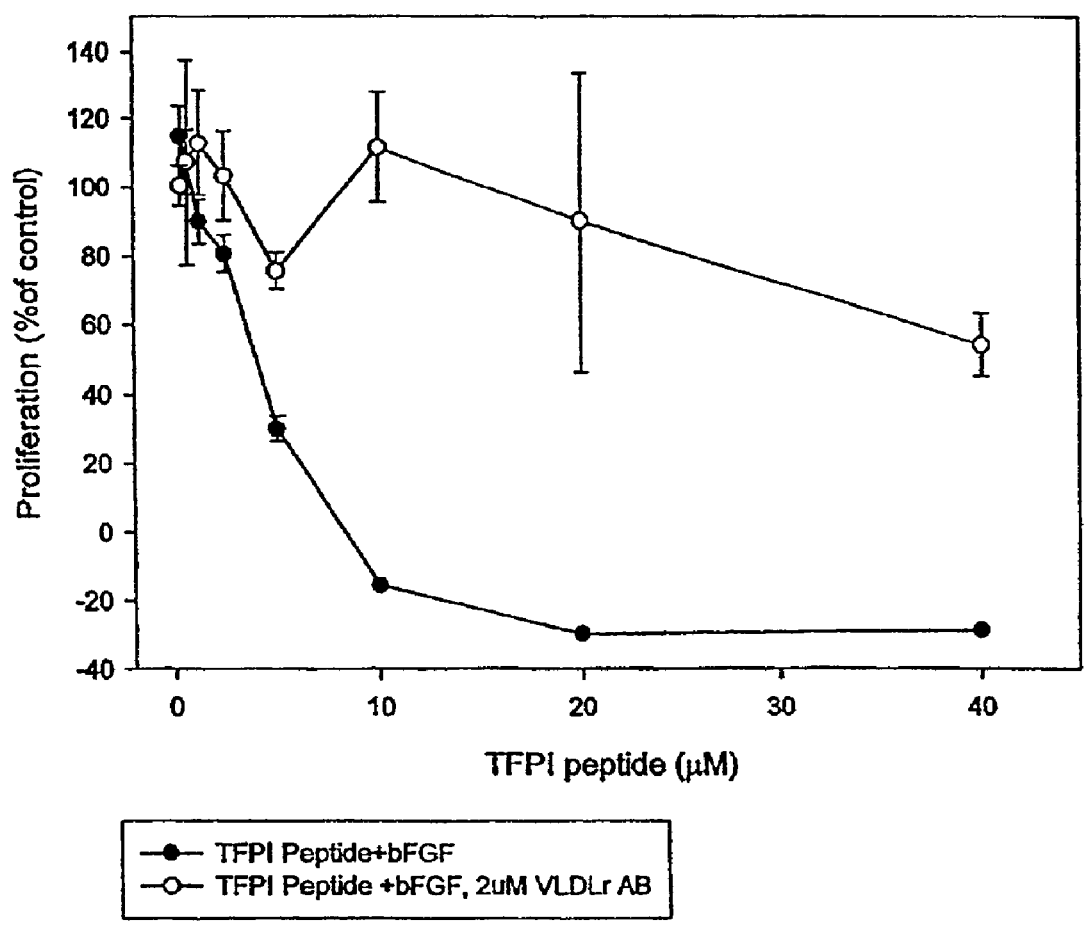
FIG. 8 is a dose response graph showing the lack of inhibition of HUVEC proliferation by the TFPI C-terminal peptide in the presence of Rab4522 (a polyclonal antibody specific for the VLDL receptor).

Whether the antiproliferative activity of the TFPI C-terminal peptide required the VLDL receptor was assessed using a specific polyclonal antibody for the VLDL receptor Rab4522. As discussed in Example 3, bFGF proliferation experiments were performed on HUVECs in the presence and absence of 2 $\mu$M Rab4522. As shown in FIG. 8, preincubation with Rab4522 blocked the activity of the TFPI C-terminal peptide suggesting that the TFPI peptide must bind to the VLDL receptor in order to inhibit cell proliferation.

Experiments were also conducted to determine if the TFPI peptide could inhibit the growth of metastatic tumors, see Example 4. It has been shown that inhibitors of endothelial cell growth and angiogenesis can be potent inhibitors of tumor growth. The antitumor activity of the TFPI C-terminal peptide was assessed in the Lewis lung carcinoma experimental metastasis model. In this model, tumor cells are injected through the tail vein, and cells then home to the lungs. On day three after inoculation treatment was initiated with the TFPI C-terminal peptide. In this way these studies determine the effect of the TFPI peptide on the growth of tumors in situ, and do not address the earlier steps in metastasis development.

Figure 9:
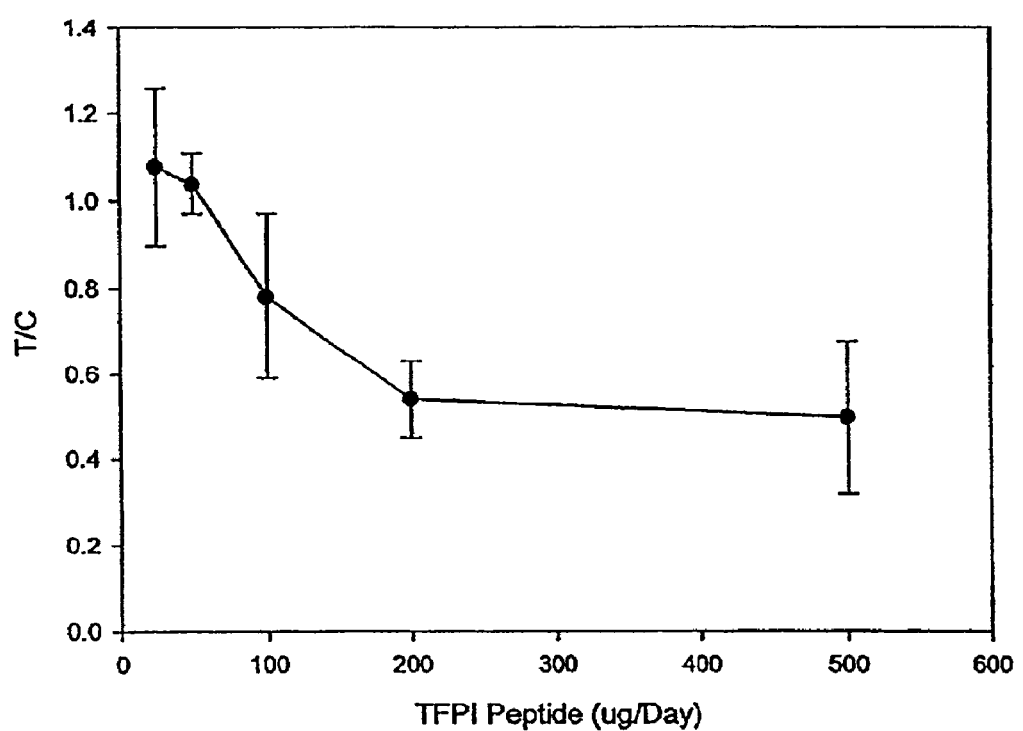
FIG. 9 is a dose response graph showing the inhibition of metastatic melanoma growth by the TFPI C-terminal peptide.

In these studies, animals were treated with increasing amounts of the TFPI C-terminal peptide daily via intraperitoneal injection. The results as shown in FIG. 9, demonstrate that the TFPI peptide is a potent inhibitor of metastatic melanoma growth. There was a dose response until the highest doses where the effect plateaus. These data demonstrate that the carboxyl terminal peptide from TFPI is a potent inhibitor of tumor growth.

Further experiments confirmed the antiangiogenic activity of the TFPI C-Terminal peptide. Example 5 demonstrated the inhibition of vessel-like structure development on spheroids.

As a result of the experiments described in the Examples, the inventors of the present invention have identified a novel application for a TFPI peptide. The peptide preferably comprises approximately the last 23 amino acids from the C-terminal region of TFPI (SEQ ID NO: 3) and is characterized in its ability to bind a VLDL receptor. The novel antiproliferative activity of this peptide is demonstrated herein by its ability to inhibit the proliferation of endothelial cells. The characteristics of this novel peptide make it an excellent candidate for use in the treatment of cancer. As demonstrated in the animal studies discussed herein, the novel C-terminal peptide is a potent inhibitor of metastatic melanoma growth and would therefore constitute a valuable component in the therapeutic intervention and management of cancer.

Peptides or Protein Fragments

Peptides or protein fragments containing antiangiogenic fragments from TFPI can be produced from the proteins described above and tested for antiproliferative activity using techniques and methods described in the Examples and known to those skilled in the art. For example, full length recombinant TFPI (rTFPI) can be produced using the Baculovirus gene expression system. Full length proteins can be cleaved into individual domains or digested using various methods such as, for example, the method described by Enjyoji et al. (*Biochemistry* 34:5725–5735 (1995)).

Alternatively, fragments are prepared by digesting the entire protein, or large fragments thereof exhibiting antiproliferative activity, to remove one amino acid at a time. Each progressively shorter fragment is then tested for antiproliferative activity. Similarly, fragments of various lengths may be synthesized and tested for anti-proliferative activity. By increasing or decreasing the length of a fragment, one skilled in the art may determine the exact number, identity, and sequence of amino acids within the protein that are required for antiproliferative activity using routine digestion, synthesis, and screening procedures known to those skilled in the art. A preferred method for producing the peptides of the present invention is T-Boc or F-Boc chemistry. See http://www.5z.com/divinfo/spps.html; see also Fields, G. B. Methods in Enzymology: Solid-Phase Peptide Synthesis Academic Press, San Diego, Volume 289 (1997).

Anti-proliferative activity is evaluated in situ by testing the ability of the fragments to inhibit the proliferation of new blood vessel cells, referred to herein as the inhibition of angiogenesis. A suitable assay is the chick embryo chorioallantoic membrane (CAM) assay described by Crum et al., *Science* 230:1375 (1985) and described in U.S. Pat. No. 5,001,116, which is incorporated by reference herein. The CAM assay is briefly described as follows. Fertilized chick embryos are removed from their shell on day 3 or 4, and a methylcellulose disc containing the fragment of interest is implanted on the chorioallantoic membrane. The embryos are examined 48 hours later and, if a clear avascular zone appears around the methylcellulose disc, the diameter of that zone is measured. The larger the diameter of the zone, the greater the anti-angiogenic activity. An additional assay used to assess antiangiogenic activity is the Matrigel assay and is described by Passaniti et al. (Passaniti et al. *Lab. Invest.* 67(4):519–28 (1992)).

The active fragment is preferably a fragment containing the final portion of the C-terminal region of TFPI comprising approximately the final 45 amino acids (SEQ ID NO: 1). More preferably, the antiproliferative fragment comprises the final 30 amino acids (SEQ ID NO: 2). Most preferably, the antiproliferative fragment comprises the final 23 amino acids (SEQ ID NO: 3). In an alternatively preferred embodiment the antiproliferative fragment comprises the final 23 amino acids of TFPI-2 (SEQ ID NO: 4).

Antibodies of Antiproliferative Protease Inhibitors

The present invention further comprises antibodies of antiproliferative protease inhibitors, such as antiangiogenic proteins and peptides, that may be used for diagnostic as well as therapeutic purposes. The antibodies provided herein are monoclonal or polyclonal antibodies having binding specificity for desired proteins and peptides. The preferred antibodies are monoclonal antibodies, due to their higher specificity for the proteins. The antibodies exhibit minimal or no crossreactivity with other proteins or peptides. Preferably, the antibodies are specific for antiangiogenic proteins and peptides such as TFPI. More preferably, the antibodies are specific for the C-terminal portion of TFPI, preferably the peptide comprising the final 45 amino acids (SEQ ID NO:1) or the peptide comprising the final 30 amino acids (SEQ ID NO:2). Most preferably the antibodies are specific for the C-terminal TFPI peptide comprising the final 23 amino acids, (SEQ ID NO:3).

Monoclonal antibodies are prepared by immunizing an animal, such as a mouse or rabbit, with a whole or immunogenic portion of a desired ligand, such as antithrombin III. Spleen cells are harvested from the immunized animals and hybridomas generated by fusing sensitized spleen cells with a myeloma cell line, such as murine SP2/O myeloma cells (ATCC, Manassas, Va.). The cells are induced to fuse by the addition of polyethylene glycol. Hybridomas are chemically selected by plating the cells in a selection medium containing hypoxanthine, aminopterin and thymidine (HAT).

Hybridomas are subsequently screened for the ability to produce monoclonal antibodies against antiangiogenic proteins and peptides. Hybridomas producing antibodies that bind to the proteins are cloned, expanded and stored frozen for future production. The preferred hybridoma produces a monoclonal antibody having the IgG isotype, more preferably the IgG1 isotype.

The polyclonal antibodies are prepared by immunizing animals, such as mice or rabbits with an antiangiogenic protein or peptide such as the TFPI C-terminal peptide described above. Blood sera is subsequently collected from the animals, and antibodies in the sera screened for binding reactivity against the peptide, preferably the antigens that are reactive with the monoclonal antibody described above.

Either the monoclonal antibodies or the polyclonal antibodies, or both may be labeled directly with a detectable label for identification and quantitation of antiangiogenic proteins and peptides in a biological as described below. Labels for use in immunoassays are generally known to those skilled in the art and include enzymes, radioisotopes, and fluorescent, luminescent and chromogenic substances including colored particles, such as colloidal gold and latex beads. The antibodies may also be bound to a solid phase to facilitate separation of antibody-antigen complexes from non-reacted components in an immunoassay. Exemplary solid phase substances include, but are not limited to, microtiter plates, test tubes, magnetic, plastic or glass beads and slides. Methods for coupling antibodies to solid phases are well known to those skilled in the art.

Alternatively, the antibodies may be labeled indirectly by reaction with labeled substances that have an affinity for immunoglobulin, such as protein A or G or second antibodies. The antibodies may be conjugated with a second substance and detected with a labeled third substance having an affinity for the second substance conjugated to the antibody. For example, the antibodies may be conjugated to biotin and the antibody-biotin conjugate detected using labeled avidin or streptavidin. Similarly, the antibodies may be conjugated to a hapten and the antibody-hapten conjugate detected using labeled anti-hapten antibody. These and other methods of labeling antibodies and assay conjugates are well known to those skilled in the art.

Sensitive immunoassays employing one or more of the antibodies described above are provided by the present invention. The immunoassays are useful for detecting the presence or amount of antiangiogenic proteins and peptides in a variety of samples, particularly biological samples, such as human or animal biological fluids. The samples may be obtained from any source in which the proteins may exist. For example, the sample may include, but is not limited to, blood, saliva, semen, tears, and urine.

The antibody-antigen complexes formed in the immunoassays of the present invention are detected using immunoassay methods known to those skilled in the art, including sandwich immunoassays and competitive immunoassays. The antibody-antigen complexes are exposed to antibodies similar to those used to capture the antigen, but which have been labeled with a detectable label. Suitable labels include: chemiluminescent labels, such as horseradish peroxidase; electrochemiluminescent labels, such as ruthenium and aequorin; bioluminescent labels, such as luciferase; fluorescent labels such as FITC; and enzymatic labels such as alkaline phosphatase, β-galactosidase, and horseradish peroxidase.

The labeled complex is then detected using a detection technique or instrument specific for detection of the label employed. Soluble antigen or antigens may also be incubated with magnetic beads coated with non-specific antibodies in an identical assay format to determine the background values of samples analyzed in the assay.

Formulations

The naturally occurring or synthetic protein, peptide, or protein fragment, containing all or an active portion of a proteinase inhibitor, namely a C-terminal peptide of TFPI, can be prepared in a physiologically acceptable formulation, such as in a pharmaceutically acceptable carrier, using known techniques. For example, the protein, peptide or protein fragment is combined with a pharmaceutically acceptable excipient to form a therapeutic composition.

Alternatively, the gene for the protein, peptide, or protein fragment, containing all or an active portion of a Kunitz-type domain, is delivered in a vector for continuous administration using gene therapy techniques. The vector may be administered in a vehicle having specificity for a target site, such as a tumor.

The composition may be in the form of a solid, liquid or aerosol. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection subcutaneously, intravenously, intra-arterially, and formulations for topical and intraocular administration. Examples of aerosol formulations include inhaler formulations for administration to the lungs.

The composition may be administered by standard routes of administration. In general, the composition may be administered by topical, oral, rectal, nasal or parenteral (for example, intravenous, subcutaneous, or intermuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (copolymers of lactic acid and glycolic acid).

The dosage of the composition will depend on the condition being treated, the particular composition used, and other clinical factors such as weight and condition of the patient, and the route of administration.

The composition may be administered in combination with other compositions and procedures for the treatment of diseases. For example, unwanted cell proliferation may be treated conventionally with surgery, radiation or chemotherapy in combination with the administration of the composition, and additional doses of the composition may be subsequently administered to the patient to stabilize and inhibit the growth of any residual unwanted cell proliferation.

Diseases and Conditions to be Treated

The methods and compositions described herein are useful for treating human and animal diseases and processes mediated by abnormal or undesirable cellular proliferation, particularly abnormal or undesirable endothelial cell proliferation, including, but not limited to, hemangioma, solid tumors, leukemia, metastasis, telangiectasia psoriasis scleroderma, pyogenic granuloma, myocardial angiogenesis, plaque neovascularization, coronary collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation. The method and composition are particularly useful for treating angiogenesis-related disorders and diseases by inhibiting angiogenesis.

The methods and compositions described herein are particularly useful for treating cancer, arthritis, macular degeneration, and diabetic retinopathy. Administration of the compositions to a human or animal having prevascularized metastasized tumors is useful for preventing the growth or expansion of such tumors.

The compositions and methods are further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Effect of TFPI C-terminal Peptide on bFGF and VEGF Stimulated Endothelial Cell Proliferation We sought to identify the domains of TFPI that were responsible for this activity. Our initial experiments were designed to assess the antiproliferative activity of a peptide consisting of the carboxyl terminal 23 amino acids of TFPI (SEQ ID NO: 3). This peptide is highly basic, and was previously identified as an important domain, which might mediate the cell surface interactions, as well as the antiproliferative activity of TFPI. The peptide was used to treat quiescent HUVECs that had been stimulated with either bFGF or VEGF.

Proliferation Assay of Endothelial Cells

HUVECs were routinely cultured to near confluency in EGM media (Clontech). The cells were trypsinized and plated in a 96-well plate at 5,000 cells per well per 100 µl EBM supplemented with 2% FCS and antibiotics. The cells were allowed to adhere to the plate for at least 12 hrs. Then, bFGF at 10 ng/ml, or VEGF at 5 ng/ml and various concentrations of TFPI peptide, or control peptide were added to the wells. The cells were cultured for 48 hrs at 37° C. in a 5% $CO_2$ atmosphere. Cell proliferation was determined using a uridine incorporation method as described by the manufacturer and confirmed by cell counting (Cell Counter Model Z1, Coulter Incorporation, Miami, Fla.). Inhibition of cell proliferation, as assessed by uridine incorporation, was calculated using the following formula:

% inhibition of proliferation=[Absorbance of bFGF-treated cells]−[Absorbance of bFGF and TFPI-treated cells]/ [Absorbance of bFGF-treated cells]−[Absorbance of untreated cells]×100

As seen in FIG. 5, the C-terminal peptide is a potent inhibitor of HUVEC proliferation. Complete inhibition was seen at doses above 20 µM, and the $IC_{50}$ for this peptide in both assays was around 5 µM. In contrast, even at doses up to 250 µM, this peptide did not inhibit the growth of two different tumor cell lines, B16 murine melanoma and EOMA hemangioendothelioma cells (FIG. 6). Control experiments were performed with a scrambled peptide. In these experiments, no inhibition of cell proliferation was seen (data not shown).

EXAMPLE 2

Interaction of TFPI C-terminal Peptide with VLDL Receptor

We had previously shown that TFPI was a ligand for the VLDL receptor, and that this interaction was necessary for the antiproliferative activity of TFPI. For this reason we sought to determine of the TFPI C-terminal peptide was a ligand for the VLDL receptor.

VLDL Receptor Binding Experiments

We measure the ability of the TFPI peptide to compete for the binding of 1 nM RAP (a well known high affinity ligand to the VLDL receptor in vivo and in vitro) to immobilized sVLDLr1-8 (the ligand binding region of the VLDL receptor). Briefly, microtiter wells were coated with either BSA or sVLDLr1-8. After blocking with 3% BSA, the wells were incubated for 1 hour at 37 C with 1 nM RAP in absence or presence of increasing amounts of the TFPI peptide. Following the incubation, wells were washed, and incubated with a polyclonal antibody against RAP for 1 hour at room temperature. Next, the wells washed and incubated with an alkaline phosphatase conjugated anti-rabbit antibody for 1 hour at room temperature. Following this incubation, the wells washed and incubated with alkaline phosphatase substrate. Next, we measured the absorbance at 405 nm.

FIG. 7 shows a competition experiment where increasing concentrations of peptide are used to block the binding of RAP to immobilized VLDLr ligand binding repeats 1–8. In this experiment the TFPI peptide is able to block binding of RAP to the VLDL receptor.

EXAMPLE 3

Effect of TFPI C-terminal Peptide Interaction with VLDL Receptor on Antiproliferative Activity We next assessed whether the antiproliferative activity of the TFPI peptide required the VLDL receptor. This was done by using a Rab4522, a specific polyclonal antibody for the VLDL receptor.

VLDL Receptor Binding Experiments

Experiments were set up identically to those outlined in Example 2 above, except these were performed using VLDL receptor specific antibodies to block the antiproliferative activity of the TFPI peptide. In these experiments, a fixed concentration (1 uM) of the rabbit polyclonal anti VLDLr IgG (R4522) was preincubated with HUVECs for 1–2 h at 37° C. After addition of VLDLr antibody, TFPI peptide and bFGF were added, and HUVEC proliferation was determined as above.

In the experiments shown in FIG. 8, bFGF proliferation experiments were performed on HUVECs in the presence of absence of 2 µM Rab4522. In this experiment preincubation with Rab4522 blocks the activity of the TFPI peptide. This suggests that the TFPI peptide must bind to the VLDL receptor in order to inhibit cell proliferation.

EXAMPLE 4

Effect of TFPI C-terminal Peptide on Growth of Metastatic Tumors

The final experiments were designed to determine if the TFPI peptide could inhibit the growth of metastatic tumors. It has been shown that inhibitors of endothelial cell growth and angiogenesis can be potent inhibitors of tumor growth. We assessed the antitumor activity of the TPFI peptide in the Lewis lung carcinoma experimental metastasis model. In this model, tumor cells are injected through the tail vein, and cells then home to the lungs. On day three after inoculation treatment is initiated with the TFPI peptide. In this way these studies determine the effect of the TFPI peptide on the growth of tumors in situ, and do not address the earlier steps in metastasis development.

Treatment of Experimental Pulmonary Tumor Metastasis

Groups of five C57BL/6J mice were injected with $5\times10^4$ LLC cells and were subsequently treated intraperitoneally with various concentrations of the TFPI peptide, scrambled control peptide or equal volume of diluent control. Treatment was initiated three days after tumor cell inoculation. Two weeks after the intravenous injection of tumor cells, the mice were sacrificed and necropsied. The lungs were removed, weighed and compared to diluent treated controls, and to normal lungs without tumors. Results were analyzed for statistical significance using the Student's t-test.

In these studies, animals were treated with increasing amounts of TFPI peptide daily via intraperitoneal injection. We show in FIG. 9 that the TFPI peptide is a potent inhibitor of metastatic melanoma growth. There was a dose response until the highest doses where the effect plateaus. These data demonstrate that the carboxyl terminal peptide from TFPI is a potent inhibitor of tumor growth.

EXAMPLE 5

Effect of TFPI C-terminal Peptide on Angiogenesis

In order to assess the effect of the TFPI C-terminal peptide on angiogenesis, sprouting assays using the peptide were conducted.

The sprouting assays used for the following studies are described in detail by Kroff and Augustin, *Journal of Cell Science*, 112:3249–3258 (1999); Kroff et al. *The FASEB Journal*, 115:447–457 (2001); and Kroff and Augustin, *The Journal of Cell Biology*, 143(5): 1341–1352 (1998).

Briefly, during angiogenesis, anastomosing capillary sprouts align to form complex three-dimensional networks of new blood vessels. The endothelial cell spheroid model used herein is a collagengel-based three-dimensional in vitro angiogenesis assay. In this assay, cell number-defined, gel-embedded endothelial cell spheroids act as a cellular delivery device, which serve as a focal starting point for the sprouting of lumenized capillary-like structures that can be induced to form complex anastomosing networks. Formation of capillary anastomoses is associated with tensional remodeling of the collagen matrix and directional sprouting of outgrowing capillaries towards each other.

Materials

Generation of Spheroids

Plasticware: non adhesive 96-well plates for suspension cultures (U-form, cat#: 650185 from Greiner, Vineland N.J.). Cells/Media: HUVEC cells grown for at least 48 hrs in the Clonetics EGM Media (supplemented with ECGS (bovine brain extract), hydrocortisone and 10% FBS), EGM Media supplemented with ECGS, hydrocortisone and 10% FBS. Solutions: Methocel Stock Solution (MSS)

Sprouting Assay

Plasticware: prewarmed 24-well plates, heat-pack. Solutions: Collagen Stock Solution (CSS), 0.2 NaOH, 50 mg/ml $NaHCO_3$. 10×HBSS with Phenolred (Sigma, Stl. Louis, Mo.), MSS/FBS mixture (70%/30%), PBS.

Generation of Spheroids

For the spheroid sprouting assay spheroids containing 750 cells are generated. EGM grown HUVECs are trypsinized and harvested in EGM media. Cell concentration is determined. For the inner 8 wells on a 24 well-plate 400 spheroids must be generated, or four 96-well plates. It is important to use u-shaped, non-adhesive 96-well plates for suspension cultures to avoid attachment of the cells to the plastic.

Pipet 150 µl of media containing 750 cells (in 80% EGM+supplements media and 20% MSS, concentration is $0.5\times10^4$ cells/ml) into the 96 well plate for suspension cultures. Per plate 15 ml containing $7.5\times10^4$ cells or for 4 plates 60 ml containing $30\times10^4$ cells supended in 80% EGM+supplements and 20% MSS are required. Incubate plates at 37 C with 5% $CO_2$ at least overnight. Check wells to see if spheroid formation is complete (1 spheroid/well).

Sprouting Assay (Procedure for 8 wells)

Harvesting the Spheroids

Place empty 24 well-plates into incubator and allow to prewarm for at least 30'. Harvest the spheroids with a multi-channel pipette and 200 µl tips with a wide orifice and collect the spheroids in a sterile reagent reservoir (from four 96-well plates). Transfer spheroids into 50 ml tubes, rinse the reservoir with PBS and transfer as well. Prepare MSS/FBS (70%/30%) solution by adding 7.5 ml FBS to 17.5 ml MSS. Mix carefully by inversion to avoid air bubbles. Spin down harvested spheroids and the MSS/FBS solution at 300 g for 3 min. Remove the supernatant and rock tube to loosen the spheroids. Cover spheroids with 4.5 ml of MSS/FBS (70%/30%) and leave at room temperature (the solution is very viscous, you will have to aspirate ~6 ml to get 4.5 ml out of the pipette). Do not mix with the spheroids, just overlay the spheroids with the MSS/FBS.

Note: the following volumes refer to the collagen lot L001 for which a 1:1 dilution with 1:1000 acetic acid is required. 4 ml of neutralized and diluted collagen solution is needed for 8 wells. Per 4 ml 1:1000 acetic acid/CSS approximately 350 µl 0.2N NaOH is required for neutralization. Use small amounts (10–20 µl/4 ml) of $NaHCO_3$ to complete neutralization (phenolred changes its color from yellow to orange).

Neutralization of Collagen

Take a new 50 ml tube and put on ice. Add 0.5 ml 10×HBSS, 2 ml 1:1000 acetic acid and 350 µl 0.2 M NaOH into the tube and mix well. The color changes to a purple-red. Add 2 ml CSS and mix well. The color changes back to a yellow-orange. Often small amounts of additional NaHCO3 are required and should be added in small steps (10–20 µl/4 ml). The color should change to orange. Keep the now neutralized collagen solution on ice.

Seeding the Spheroids

Place heat-pack in microwave and irradiate briefly (15s). It should be a little bit warmer than body-temperature. Take a 1000 µl pipette and cut the blue tip by 3 mm in a sterile fashion. Place prewarmed 24-well plate onto the heat pack. Transfer 4 ml of the neutralized collagen solution to the MSS/FBS mixture. Mix very well with the blue pipette tip (1 ml). The mixture has to become homogenous, avoid bubble formation. Transfer 1 ml of the collagen-spheroid mixture into each of the 8 inner wells of the 24-well plate. Transfer plate immediately into the incubator and let polymerize for at least 30 min.

Layer 200 µl of DMEM, 10% FBS media containing the stimulators and or inhibitors on top of the gel (Cave: Stimulators/Inhibitors have to be at a 6-fold concentration in the media which is layered on top of the gel). A negative (no growth factor) and a positive control (growth factor, but no inhibitor) is recommended.

For evaluation, take pictures of representative spheroids after 24/48 hrs and eventually quantify the average cumulative length of the sprouts per spheroid. Avoid evaluating spheroids which came in direct contact with the plastic well since they will disintegrate and/or change growth pattern.

Preparation of Stock Solutions

Methocel stock solution (MSS):

The preparation of methocel stock solution is very critical. If the concentration of methocel is too low or the solution is containing methylcellulose debris, single cells will stick to the wall and several small spheroids are formed in each well. Use methylcellulose from Sigma (cat#: m-0512, 4000 centipoises). The methocel stock solution should have an extremly high viscosity. The basal medium used here to dissolve the methylcellulose is the Cascade 200 media with NO growth supplements except Pen-strep and L-glutamine.

Autoclave the pure powder (6 g) in a 500–1000 ml flask containing a large magnetic stirbar (the methylcellulose powder is resistant to this procedure).

The autoclaved methylcellulose is dissolved in preheated 250 ml basal medium 200 (60° C.) for 20 min (using the magnetic stirrer). Thereafter, 250 ml basal 200 medium (room temperature) is added to a final volume of 500 ml and the whole solution is mixed for 1–2 h (4° C.). The final stock solution is aliqoted and cleared by centrifugation (5000 g, 2 h, room temperature). Only the clear highly viscous supernatant should be used for the spheroid assay (about 90–95% of the stock solution).

Collagen Stock Solution (CSS):

To prepare a collagen stock solution 250 ml steril filtered acetic acid diluted 1:1000 in aqua dest. (cell culture quality), 2 rat tails (stored at –20° C.), 2×500 ml 70% Ethanol are needed.

Place the rat tails for 20 min in 70% ethanol, remove the skin. Wash the naked tails in ethanol. Break each second (depends on the length of the tails) joint and extract the tendons. Be sure to get clean tendons without attached connective tissue. Take all the tendons and place them in the second 500 ml clean ethanol for 20 min. Dry the tendons under the lamina airflow for 20–30 min. Put the tendons in 250 ml acetic acid (see above) and place them in the refrigerator for 48 hours shaking the solution at least two times each day.

Aliquot the final solution in autoclaved tubes and centrifuge them at 4° C. at 17.000 g for 1 h. Collect the clear supernatant. Be sure not to collect the debris. The clear supernatant/collagen stock solution can be stored in the refrigerator for at least 6 months.

To determine the right collagen concentration and get the dilution factor necessary, carefully mix 4 ml of the stock solution with 0.5 ml 10×HBSS and keep the mixed solution on ice for at least 15 min. In most cases the collagen concentration of the stock solution is too high and the mixed solution will become a gel. In that case dilute the collagen stock solution (use 1:1000 sterile filtered acetic acid) and mix it with 10×HBSS as described above. Repeat diluting the stock solution until the mixed solution stays liquid. The current Lot L001 has to be diluted 1:1.

To keep the EC baseline sprouting level low, it is advisable to prepare the stock solution at least 4 weeks before use (freshly prepared collagen by itself has the capability to induce sprouting of EC).

Results

FIG. 13(a-c) demonstrates that increasing amounts of C-terminal peptide inhibit the sprouting of vessel-like structures on spheroids in comparison to normal growth.

FIG. 14(a-d) demonstrates the effect of the C-terminal peptide in the presence and absence of a VLDL antibody. As shown in FIG. 15b, inhibition of vessel development is markedly decreased in the presence of the VLDL antibody.

Figure 15:
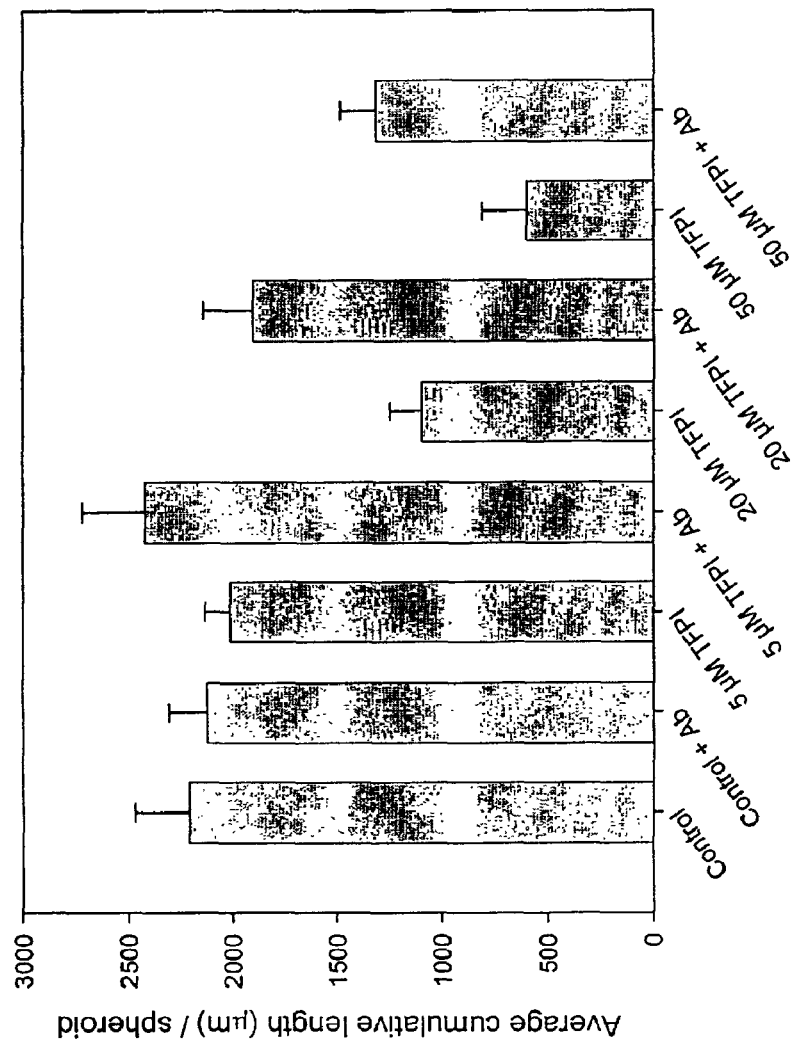
FIG. 15 is a graph showing the effect of the TFPI C-terminal peptide on the cumulative length of spheroid vessels in the presence of varying peptide amounts, and in the presence of varying peptide amounts together with VLDL antibody. The vertical axis provides average cumulative length (µm)/spheroid vessels, and the horizontal axis identifies the environment in which the assay was conducted.

FIG. 15 shows the effect of the C-terminal peptide on the cumulative length of spheroid vessels in the presence of varying peptide amounts, and in the presence of varying peptide amounts together with VLDL antibody.

Conclusion

As demonstrated by the results of the sprouting assay experiments above, the C-terminal peptide of the present invention is effective in inhibiting angiogenesis. One can make this conclusion based on the extrapolation of results from the sprouting assays to angiogenic processes based on the teachings of Kroff and Augustin (see above). Furthermore, since spheroid development was decreased in the presence of the TFPI C-terminal peptide and not decreased in the presence of the peptide together with the VLDL antibody, additional evidence is provided supporting the theory that this peptide exerts its effects via the VLDL receptor.

It should be understood, of course, that the foregoing relates only to preferred embodiments of the present invention and that numerous modifications or alterations may be made therein without departing from the spirit and the scope of the invention as set forth in the appended claims.

We claim:

1. A method of inhibiting endothelial cell proliferation in a human or animal comprising, administering to the human or animal a sufficient amount of a composition comprising a tissue factor pathway inhibitor C-terminal peptide to inhibit the undesirable endothelial cell proliferation wherein the C-terminal peptide comprises at least 23 C-terminal residues of SEQ ID No. 5 or SEQ ID No. 6.

2. The method of claim 1 wherein the endothelial cell proliferation occurs during an angiogenesis-related disease.

3. The method of claim 2, wherein the angiogenesis-related disease is a disease selected from the group consisting of hemangioma, solid tumors, leukemia, metastasis, telangiectasia psoriasis scleroderma, pyogenic granuloma, myocardial angiogenesis, plaque neovascularization, coronary collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation.

4. The method of claim 1 wherein administration of the composition inhibits angiogenesis.

5. The method of claim 1 wherein the tissue factor pathway inhibitor is a protein having the amino acid sequence set forth in SEQ ID NO: 5.

6. The method of claim 5 wherein the C-terminal peptide is selected from the group consisting of SEQ ID NO: 1, SEQ ID NO: 2 and SEQ ID NO: 3.

7. The method of claim 5 wherein the C-terminal peptide consists of SEQ ID NO: 3.

8. The method of claim 1 wherein the tissue factor pathway inhibitor is a protein having the amino acid sequence set forth in SEQ ID NO. 6.

9. The method of claim 8 wherein the C-terminal peptide consists of SEQ ID NO: 4.

10. The method of claim 1 wherein the composition further comprises a pharmaceutically acceptable excipient, carrier or sustained-release matrix.

11. A method for treating an angiogenesis-related disease comprising, administering to a human or animal a sufficient amount of a composition comprising a tissue factor pathway inhibitor C-terminal peptide to inhibit endothelial cell proliferation wherein the C-terminal peptide comprises at least 23 C-terminal residues of SEQ ID No. 5 or SEQ ID No. 6.

12. The method of claim 11, wherein the angiogenesis-related disease is a disease selected from the group consisting of hemangioma, solid tumors, leukemia, metastasis, telangiectasia psoriasis scleroderma, pyogenic granuloma, myocardial angiogenesis, plaque neovascularization, coronary collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation.

13. The method of claim 11 wherein the tissue factor pathway inhibitor is a protein having the amino acid sequence set forth in SEQ ID NO. 5.

14. The method of claim 13 wherein the C-terminal peptide is selected from the group consisting of SEQ ID NO: 1, SEQ ID NO: 2 and SEQ ID NO: 3.

15. The method of claim 14 wherein the C-terminal peptide consists of SEQ ID NO: 3.

16. The method of claim 11 wherein the tissue factor pathway inhibitor is a protein having the amino acid sequence set forth in SEQ ID NO. 6.

17. The method of claim 11 wherein the C-terminal peptide consists of SEQ ID No. 4.

18. The method of claim 11 wherein the composition further comprises a pharmaceutically acceptable excipient, carrier or sustained-release matrix.

* * * * *